United States Patent
Mackay et al.

[11] Patent Number: 6,165,738
[45] Date of Patent: Dec. 26, 2000

[54] EXPRESSION IN YEAST OF ANTIGENICALLY ACTIVE, RECOMBINANT HYBRID GLUTAMIC ACID DECARBOXYLASE

[75] Inventors: Ian Reay Mackay, Malvern; Merrill Joy Rowley, Camberwell; Paul Zev Zimmet, Toorak, all of Australia; Brian Corner, St. Paul, Minn.; Ruby Law, Caulfield, Australia; Khay-Lin Teoh, Singapore, Singapore

[73] Assignees: Montech Medical Developments Pty. Ltd., Melbourne; Rondole Pty. Ltd., Hobart, both of Australia

[21] Appl. No.: 09/341,824

[22] PCT Filed: Jan. 21, 1998

[86] PCT No.: PCT/AU98/00025

§ 371 Date: Sep. 13, 1999

§ 102(e) Date: Sep. 13, 1999

[87] PCT Pub. No.: WO98/31819

PCT Pub. Date: Jul. 23, 1998

[30] Foreign Application Priority Data

Jan. 21, 1997 [AU] Australia ............... PO 4685

[51] Int. Cl.[7] .................................................. G01N 33/53
[52] U.S. Cl. .................. 435/7.6; 435/232; 435/320.1; 435/252.3; 435/419; 435/325; 435/254.2; 435/254.21; 435/254.23; 530/350; 536/23.1; 536/23.2; 424/94.5
[58] Field of Search .................... 435/233, 320.1, 435/232, 252.3, 419, 254.2, 325, 254.21, 254.23; 530/350; 536/23.1, 23.2; 424/94.5

[56] References Cited

U.S. PATENT DOCUMENTS 5,821,334 10/1998 Powers ..................... 530/350

OTHER PUBLICATIONS

K. Daw et al., "Diabetes 44", *Two Distinct Glutamic Acid Decarboxylase Auto–Antibody Specificities in IDDM Target Different Epitopes*, pp. 216–220, (1995).

K. Daw et al., "J. Immunol. 156(2)", *Glutamic Acid Decarboxylase Autoantibodies in Stiff–Man Syndrome and Insulin–Dependent Diabetes Mellitus Exhibit Similarities in Epitope Recognition*, pp. 818–825, (1996).

B. Ziegler et al., "Acta Diabetol 33", *Murine Monoclonal Glutamic Acid Decarboxylase (GAD) 65 Antibodies Recognise Autoimmune–Associated GAD Epitope Regions Targeted in Patients with Type 1 Diabetes Mellitus and Stiff–Man Syndrome*, pp. 225–231, (1996).

Bu et al. Two human glutamate decarboxylases, 65–kDa GAD and 67–kDa GAD, ar encoded by a single gene. PNAS (1992) 89:2115–2119, Mar. 1992.

GenBank Accession No. NP_000808, Mar. 1992.

GenBank Accession No. Q05329, Mar. 1992.

*Primary Examiner*—Ponnathapu Achutamurthy
*Assistant Examiner*—Kathleen Kerr
*Attorney, Agent, or Firm*—Foley & Lardner

[57] ABSTRACT

An antigenically active hybrid glutamic acid decarboxylase (GAD) comprising an amino-terminal moiety derived from the GAD67 isoform linked directly or indirectly with a middle and carboxy-terminal moiety derived from the GAD65 isoform, and production thereof as a recombinant protein by expression in eukaryotic host cells, particularly yeasts.

23 Claims, 10 Drawing Sheets

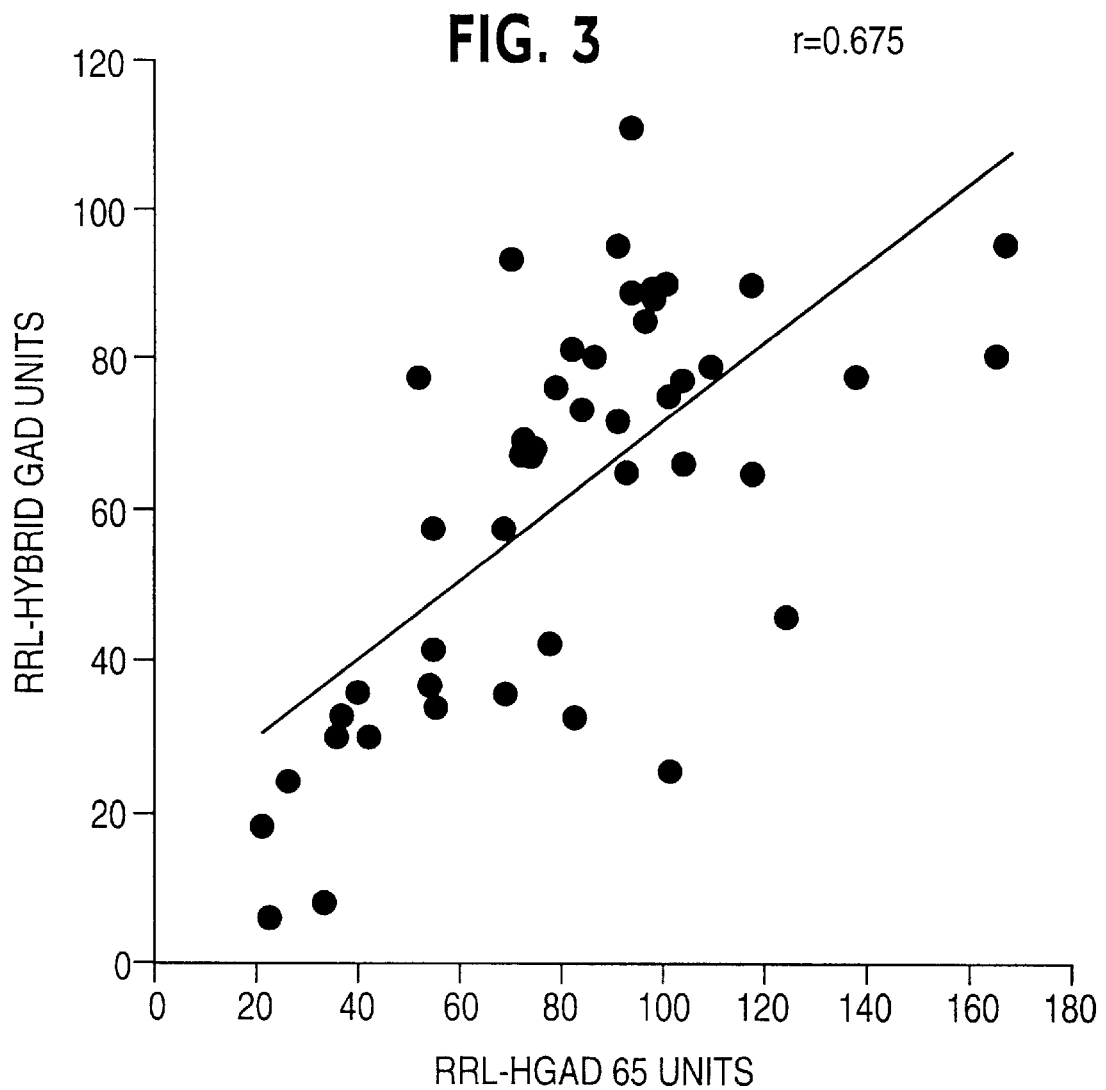

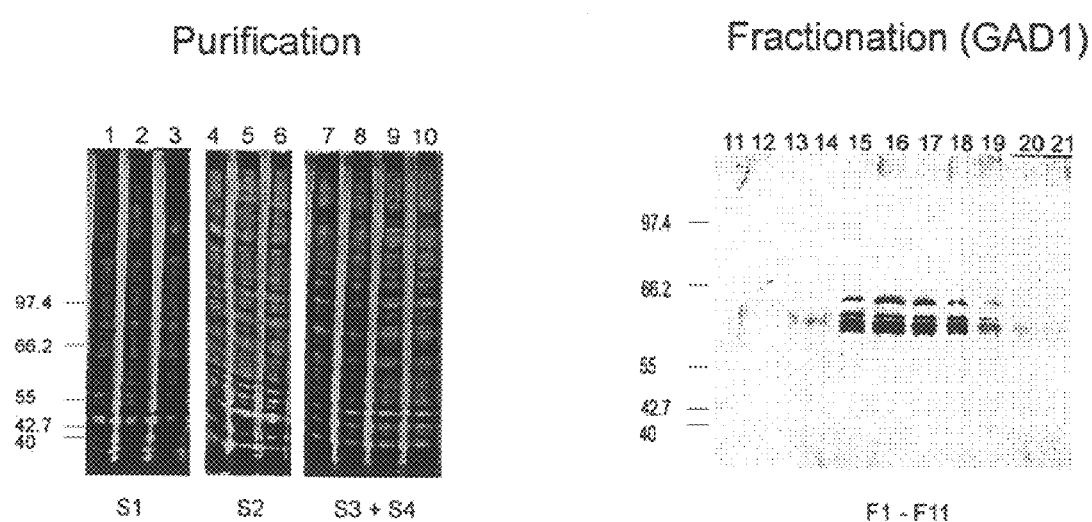

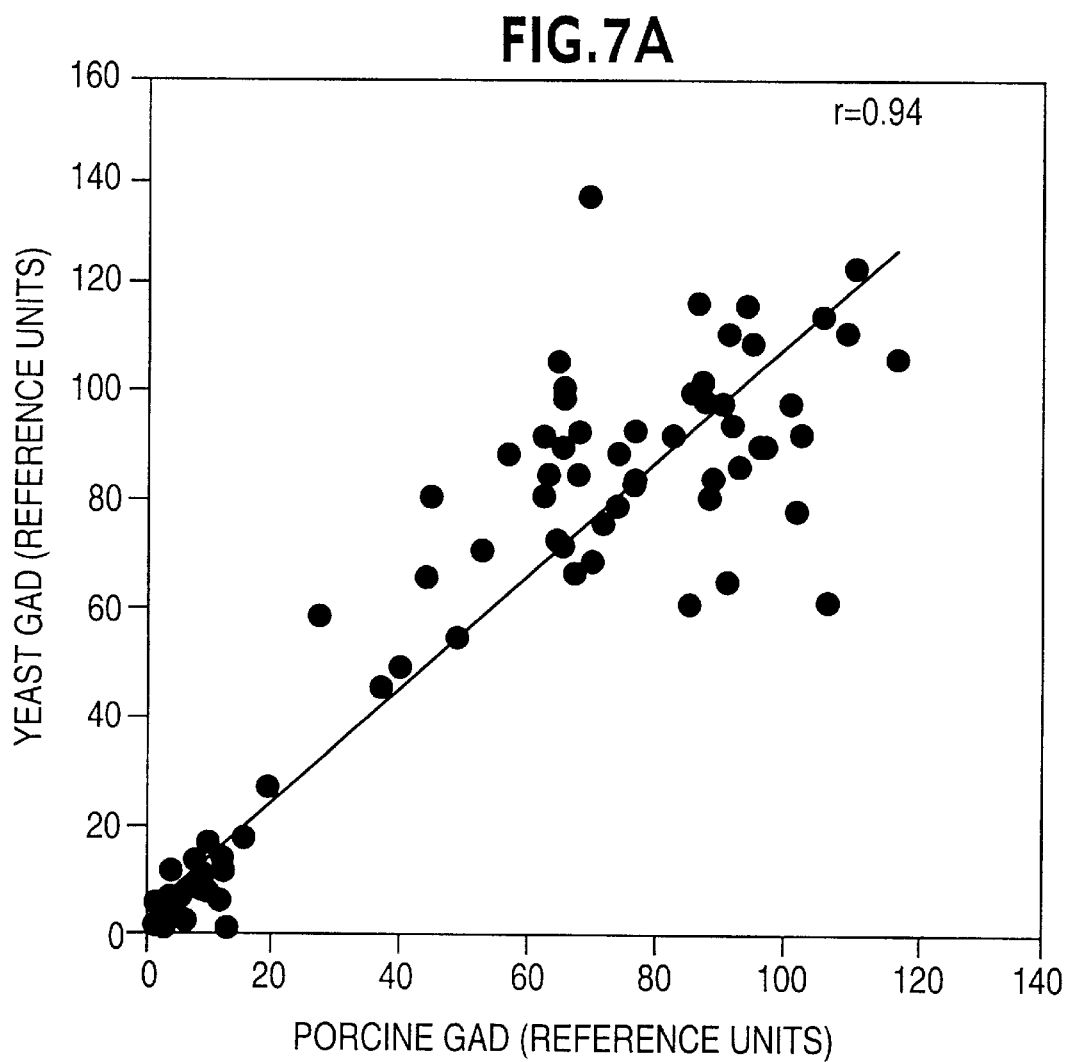

EXPRESSION IN YEAST OF ANTIGENICALLY ACTIVE, RECOMBINANT HYBRID GLUTAMIC ACID DECARBOXYLASE

FIELD OF THE INVENTION

This invention relates to the production of an antigenically active hybrid glutamic acid decarboxylase (GAD) molecule as a recombinant protein by expression in eukaryotic host cells, particularly yeasts, and to the use of this recombinant hybrid GAD in the diagnosis and presymptomatic detection of insulin-dependent (Type 1) diabetes mellitus (IDDM). The invention also relates to the use of this hybrid GAD molecule to inhibit or prevent the occurrence of IDDM in individuals who are diagnosed or detected as having presymptomatic IDDM.

BACKGROUND OF THE INVENTION

Insulin dependent diabetes mellitus (DDM) is an autoimmune disease in which there is a characteristic immunological reactivity to a limited set of tissue-specific cytoplasmic autoantigens of pancreatic islet beta cells. Reactivity to one of these autoantigens, glutamic acid decarboxylase (GAD; EC 4.1.1.15), is virtually unique to the disease, the rare exceptions being the neurological disorder, Stiff man syndrome (Solimena et al., 1990; Baekkeskov et al., 1990), and the polyendocrine syndrome Types 1 and 2. Glutamic acid decarboxylase catalyses the conversion of L-glutamic acid to γ-aminobutyric acid (GABA) and carbon dioxide (Erlander et al., 1991). GABA is a major inhibitory neurotransmitter, and hence most research on GAD until recently had concentrated on the role of this enzyme in neural functioning. A new direction developed with the recognition that antibodies to GAD are prevalent in IDDM (Baekkeskov et al., 1990).

GAD exists as 2 isoforms denoted by their calculated molecular weights as GAD65 and GAD67. These differ according to their subcellular location (Erdo and Wolff, 1990; Faulkner-Jones et al., 1993), chromosomal location (Erlander et al. 1991; Karlsen et al., 1991; Bu et al., 1992; Michelsen et al., 1991), amino acid sequence (Bu et al., 1992) and cofactor interactions (Erlander and Tobin, 1991) but have close homology, in man 65% identity and 80% similarity. The greatest divergence between the isoforms occurs in the first 100 amino acids (Bu et al. 1992). The availability of cDNA clones encoding the two GAD isoforms has allowed the expression of these in various systems, including bacteria (Kaufman et al., 1992), Sf9 insect cells using the baculovirus vector (Seissler et al., 1993; Mauch et al., 1993), COS7 monkey cells (Velloso et al., 1993), baby hamster kidney cells (Hagopian et al., 1993), yeast (Powell et al, 1995) and by in vitro translation using rabbit reticulocyte lysate (RRL) (Petersen et al., 1994; Ujihara et al., 1994; Grubin et al., 1994). In addition, a modified GAD65 without the hydrophobic amino acids 245 inclusive of the N-terminal region has been expressed in yeast (Powell, et al., 1996).

The identification of GAD as a major autoantigen of IDDM has led to the extensive use of this antigen in immunoassays for the accurate diagnosis and prediction of IDDM in at-risk populations. Such studies have shown that antibodies to GAD are detectable in patients up to 10 years before the early onset of clinical symptoms (Baekkeskov et al., 1987, Atkinson et al., 1990; Rowley et al., 1992; Chen et al., 1993; Tuomilehto et al., 1994; Myers et al., 1996). These assays have employed autoantigenic GAD derived from two major sources. One source is animal materials, most commonly porcine brain, purified by affinity chromatography, and labelled with radioactive iodine. The other source is in vitro transcription and translation of the cloned human GAD65 gene, using rabbit reticulocyte lysate (RRL) which produces biosynthetically labelled GAD suitable for radioimmunoprecipitation (RIP) assays (Guazzaroti et al., 1995). Expression from RRL has been widely used in diagnostic assays for anti-GAD in human sera but the in vitro expression system has limitations in that only very small amounts, in the order of picomoles, of GAD are produced and the process is very costly. Bacterial expression does not appear to yield GAD that is amenable to use in diagnostic assays, and yields from mammalian cells are unsuitably low. Several authors have presented evidence that the GAD must be in a particular conformation to be reactive with antibodies in IDDM since IDDM sera generally do not show reactivity with GAD in Western blotting under denaturing conditions, yet show potent reactivity under non-denaturing conditions (Rowley et al., 1992; Tuomi et al., 1994, Myers et al., 1996); the GAD conformation that is recognised by the majority of IDDM sera is sensitive to exposure to reducing agents such as β-mercaptoethanol, since GAD that has been thus treated loses reactivity (Tuomi et al., 1994). It is also recognised that antibodies to GAD65 in IDDM react with particular epitopes on the molecule that lie in the mid-region and C-terminal region of the molecule. Fusions of cDNAs that encode particular sequences of GAD65 and GAD67 have been created as "chimeric" proteins to establish epitope recognition (Daw and Powers, 1995).

Assays using immunoprecipitation and either affinity purified porcine brain GAD (Rowley et al., 1992) or recombinant GAD (Kaufman et al., 1992; Seissler et al., 1993; Mauch et al., 1993; Velloso et al., 1993; Hagopian et al., 1993; Petersen et al., 1994; Ujihara et al., 1994; Grubin et al., 1994) have revealed that 70–80% of IDDM sera contain autoantibodies to GAD65, whereas only 8–25 % contain antibodies to GAD67. The autoantibodies in Stiff-man syndrome react with GAD by immunoblotting under reducing conditions (Solimena et al., 1990), whereas autoantibodies to GAD in IDDM seldom do so (Baekkeskov et al., 1990), and are thought to recognise a conformational epitope (Tuomi et al., 1994). Epitopes have been mapped by examining the reactivity by immunoprecipitation of IDDM sera against truncated polypeptides of GAD65, with one major IDDM associated epitope located to the middle and carboxy terminal domains of GAD65 (Kaufman et al., 1992; Richter et al., 1993; Ujihara et al., 1994). More recent mapping for epitopes for anti-GAD suggests the presence of two discontinuous epitopes, one within amino acids 244 to 433, and the other within amino acids 451 to 570 (Daw and Powers, 1995). Curiously, whilst antigenically active regions of GAD65 and GAD67 are highly homologous, GAD65 is the isoform with which autoantibodies are predominantly reactive.

The further development of diagnostic assays for IDDM would greatly benefit from a more accessible source of large amounts of recombinant GAD that would be free of the possible biohazards associated with mammalian sources. Furthermore, the search for disease-associated epitopes of GAD would be facilitated by the availability of a simple system with which to carry out site-specific mutagenesis and deletion studies. The requirement for GAD to be in a particular conformation has hindered prior efforts to use recombinant DNA technology to produce large quantities of antigenically active GAD. Although the use of *E. coli* expression systems is reported to produce enzymatically active GAD (Kaufman et al., 1992), published reports on the utility of bacterially-expressed antigenically active GAD for immunoassays are scarce and, as stated above, it is the experience of the present inventors that this material performs less effectively in radioimmunoprecipitation tests with IDDM sera than does GAD expressed in other systems. The preferred expression system should be capable of producing not only large amounts of GAD, but also GAD that is in an appropriate conformation to be recognised by IDDM sera.

SUMMARY OF THE INVENTION

In one aspect, the present invention provides a hybrid glutamic acid decarboxylase (GAD) which comprises an amino-terminal moiety derived from the GAD67 isoform linked directly or indirectly with a middle and carboxy-terminal moiety derived from the GAD65 isoform.

This hybrid molecule, which may also be referred to as a chimeric molecule, is referred to herein as "hybrid GAD67/65". The generation of this hybrid molecule is based on the reported location of autoimmune epitopes in the middle and carboxy-terminal moieties of GAD65, and observations by the present inventors that the amino-terminal moiety of the cDNA of GAD67 is more amenable than the cDNA of GAD65 to insertion into vectors appropriate to expression of recombinant proteins.

As used herein, references to an "amino-terminal moiety" refer to a moiety comprising amino acid 1 to amino acid 90–105, more particularly amino acid 1 to amino acid 95–101. Similarly, references herein to a "middle and carboxy-terminal moiety" refer to a moiety comprising of amino acid 90–105 to amino acid 585, more particularly amino acid 95–101 to amino acid 585. In the particularly preferred embodiment of the present invention, the hybrid GAD67/65 molecule comprises GAD67(1–101)/GAD65 (96–585).

Preferably, the amino-terminal GAD67 moiety is fused or linked directly to the middle and carboxy-terminal GAD65 moiety, however these moieties may optionally be linked indirectly through a linker moiety of from 1 to 50, preferably from 1 to 20, and more preferably from 1 to 5, amino acid residues.

The hybrid GAD67/65 molecule of this invention may also comprise other moieties fused or otherwise coupled thereto at either end of the molecule, for example moieties to assist in purification of the hybrid GAD67/65 molecule when produced as a recombinant protein, such as a glutathione-S-transferase (or GST) moiety, a β-galactosidase moiety, or a hexa-His moiety.

In another aspect, the present invention provides an isolated nucleic acid molecule, preferably a DNA molecule, comprising a nucleic acid sequence encoding a hybrid GAD67/65 molecule as broadly described above. Preferably, the sequence comprises a fusion of cDNA sequences which encode GAD67 (1–101) and GAD65 (96–585).

Such a nucleic acid molecule may comprise a recombinant DNA molecule, a recombinant DNA cloning vehicle or vector, or a host cell, preferably a eukaryotic host cell, comprising a nucleic acid sequence encoding the hybrid GAD67/65 molecules.

The present inventors have found that the hybrid GAD67/65 molecule can be expressed in a bacterial (*E. coli*) system to provide good yields of enzymatically active GAD, but immunoreactivity of the bacterially expressed hybrid GAD67/65 is not ideal. Accordingly, expression in a eukaryotic host cell, particularly a yeast species such as *Saccharomyces cerevisiae, Pichia pastoris, Kluyveromyces lactis, Hansenula polymorpha,* or *Schizosaccharonyces pombe,* is preferred.

Thus, in a preferred aspect, the present invention provides a method for the preparation of the hybrid GAD67/65 molecule which comprises expression of a nucleic acid sequence encoding the hybrid GAD67/65 molecule in a eukaryotic host cell, particularly a yeast cell such as *S. cerevisiae,* and recovery of the expression product.

The invention also extends to recombinant hybrid GAD67/65 produced by expression in a host cell, particularly in a yeast or other eukaryotic host cell, as described above.

Suitable expression control sequences an d host cell cloning vehicle or vector combinations for expression of recombinant proteins in eukaryotic host cells, particularly in yeasts such as *S. cerevisiae* and other eukaryotic host cells, are well known in the art, and are described by way of example in Sambrook et al. (1989) and by Sudbery (1996).

Recombinant hybrid GAD67/65 in accordance with the present invention may be used advantageously in place of purified native or recombinant GAD65 in the diagnosis and presymptomatic detection of IDDM in humans or non-human mammals using assay techniques previously described.

Accordingly, in yet another aspect, the present invention provides a method for the diagnosis and presymptomatic detection of IDDM in a patient characterised in that hybrid GAD67/65 as broadly described above is used to detect autoantibodies to GAD in a serum or other sample taken from the patient.

In a further aspect, the present invention provides a method of treatment to inhibit or prevent the occurrence of IDDM in a patient having presymptomatic IDDM, which comprises administration to the patient of an effective amount of hybrid GAD67/65 as described above. Preferably, the hybrid GAD 67/65 is administered by the mucosal route, most preferably by oral administration.

This method of treatment may be used to inhibit or prevent IDDM when detected in a patient in a preclinical state (i.e. presymptomatic IDDM) by immunoassays for autoantibodies or other diagnostic methods. Broadly, the objective of the treatment is to re-establish normal immune tolerance and thereby abrogate the autoimmune process that gives rise to IDDM. Accordingly, references herein to "inhibit" or "inhibition", or to "prevent" or "prevention" are intended to refer to modulation of the state of autoimmunity affecting pancreatic islet cells of the patient by administration of the hybrid GAD67/65 in such a way and under such conditions as to reinduce a state of immune tolerance ("tolerogenesis") to autoantigenic constituents of pancreatic islet cells.

As used throughout this specification, the term "patient" includes both humans and non-human mammals. Preferably, the patient is a human. It is to be understood, however, that the diagnostic and therapeutic methods of the present invention are also applicable in non-human mammals such as livestock, companion animals, laboratory test animals and captive wild animals. It is to be understood that livestock animals encompass animals such as horses, cattle, sheep, goats, donkeys and pigs, companion animals include dogs and cats of all varieties, laboratory test animals include mice, rats, guinea pigs and rabbits, and caputred wild animals include for example monkeys, kangaroos etc.

In yet another aspect, the present invention provides the use of hybrid GAD67/65 as broadly described above, in the manufacture of a pharmaceutical or veterinary composition for treatment to inhibit or prevent the occurrence of IDDM in a patient having presymptomatic IDDM.

The invention also provides a pharmaceutical or veterinary composition for use in treatment to inhibit or prevent the occurrence of IDDM in a patient having presymptomatic IDDM, which comprises hybrid GAD67/65 as broadly described above, together with one or more pharmaceutically acceptable carriers and/or diluents.

The formulation of such pharmaceutical or veterinary compositions is well known to persons skilled in this field. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically active substances is well known in the art, and it is described, by way of example, in Remington's Pharmaceutical Sciences, 18th Edition, Mack Publishing Company, Pennsylvania, USA. Except insofar as any conventional media or agent is incompatible with the active component, use thereof in the compositions of the present invention is contemplated. Supplementary active ingredients can also be incorporated into the compositions.

It is especially advantageous to formulate compositions in dosage unit form for ease of administration and uniformity of dosage. Dosage unit form as used herein refers to physically discrete units suited as unitary dosages for the human subjects to be treated; each unit containing a predetermined quantity of active component calculated to produce the desired therapeutic effect in association with the required pharmaceutical carrier and/or diluent. The specifications for the novel dosage unit forms of the invention are dictated by and directly dependent on (a) the unique characteristics of the active component and the particular therapeutic effect to be achieved, and (b) the limitations inherent in the art of compounding such an active component for the particular treatment.

A variety of administration routes are available. The particular mode selected will depend, of course, upon the particular condition being treated and the dosage that is determined to provide for optimal therapeutic efficacy. The methods of this invention, generally speaking, may be practised using various modes of administration that are medically acceptable, meaning any mode that allows for mucosal contact with the active component of the invention without causing clinically unacceptable adverse effects. Mucosal administration, including the oral, nasal or intestinal routes, is preferred.

Optimal formulations for tolerogenic preparations of hybrid GAD 67/65 in accordance with the present invention, for example simple aqueous or salt solutions or other pharmaceutical compositions that are effective when administered by a mucosal route, may be readily determined by routine trial and experiment. Suitable formulations allow for the reestablishment of natural tolerance to the GAD molecule and thereby abrogate the harmful autoimmune reaction as discussed above.

Throughout this specification, unless the context requires otherwise, the word "comprise", or variations such as "comprises" or "comprising", will be understood to imply the inclusion of a stated integer or group of integers but not the exclusion of any other integer or group of integers.

DETAILED DESCRIPTION OF THE INVENTION

In accordance with the present invention, a novel hybrid form of GAD has been created, in one particular embodiment by expression of a nucleic acid sequence which is a fusion between the cDNA that encodes amino acids 1–101 of the human GAD67 protein and the cDNA that encodes amino acids 96–585 of the human GAD65 protein. This hybrid GAD67/65 has been expressed constitutively under the control of the highly active phosphoglycerate kinase promoter (PGKI) in the yeast S. cerevisiae. Thus, it has been demonstrated that substantial levels of an enzymatically active hybrid GAD can be readily produced in yeasts, such as S. cerevisiae. Most significantly, this hybrid GAD could be purified by a single affinity chromatography step, and the purified hybrid GAD had the appropriate conformation to be highly reactive with sera of patients with IDDM, when such sera contain anti-GAD. The quantity of purified protein obtained in small scale preparations, 0.3–0.5 mg/liter, was ample for detailed studies at the molecular level. Larger quantities are readily obtainable by increasing the capacity of the fermentation vessels and increasing the capacity of the affinity column used, since there is no limitation in the supply of resources using the recombinant yeast. The ability to propagate yeast in large quantities at low cost is a great advantage over other mammalian expression systems. Being eukaryotic, the yeast system is superior to the prokaryotic expression systems such as E. coli in terms of retention of post-translational modifications.

The N-terminal region of GAD65 is palmitoylated and hence is very hydrophobic, and it is likely that this makes the purified polypeptides stick to surfaces with which it comes in contact. This is a distinct disadvantage in the preparation of recombinant GAD65. In the case of hybrid GAD67/65, the N-terminal hydrophobic region of GAD65 is replaced by that of GAD67 which is more hydrophilic in nature. When this hybrid GAD was synthesised by in vitro transcription and translation in rabbit reticulocyte lysate in the presence of $^{35}$S-methionine, the resulting product was shown to contain comparable reactivities to purified porcine GAD in radio-immunoprecipitation assays using IDDM sera. Therefore, the utility of expressing the hybrid GAD in yeast is three fold: it is enzymatically highly active, it is immunologically potent for IDDM sera, and it is far more readily recoverable during purification.

It will be appreciated that in addition to the affinity chromatography procedures described in detail herein, other appropriate protein purification procedures which are well known in the art may also be used to produce a purified hybrid GAD67/65 product suitable for use in diagnostic immunoassays, or for use in treatment of a patient to inhibit or prevent IDDM by induced tolerogenesis as described above, for example, in an orally delivered pharmaceutical composition.

Further features of the present invention are more fully described in the following Examples. It is to be understood, however, that this detailed description is included solely for the purposes of exemplifying the present invention, and should not be understood in any way as a restriction on the broad description of the invention as set out above.

BRIEF DESCRIPTION OF THE DRAWINGS

FIG. 3. Correlation of the reactivity of IDDM sera, detected by immunoprecipitation, between RRL expressed human brain GAD65 and hybrid GAD67/65. The correlation was significant (p=0.002).

FIG. 6 Analysis of hybrid GAD67/65 purified from yeast lysates. Yeast lysate collected from various stages of clarification during purification were studied as described (Methods). S1–4 are shown in lanes 1–3, 4–6, 7–9 and 10, respectively. F1–11 shown in lanes 11–21 are the first 11 fractions (1 ml volume) collected during elution of hybrid GAD from the GAD-1 affinity column. The yeast lysates studied were prepared from YRD15 (lanes 1, 4 and 7), YpAS-1 (lanes 2, 5 and 8); and YGAD-2 (lanes 3, 6, 9 and 10). FIG. 6A is a Western Blot analysis using GAD-6 and FIG. 6B is a silver staining analysis. 7.5% acrylamide was used for the SDS-PAGE.

FIG. 7 B. Comparison of yeast hybrid GAD67/65 retained for 18 months at −20° C. and purified porcine brain GAD by radioimmunoprecipitation (RIP). The sera tested were a randomly derived collection from patients with diabetes mellitus, and results are expressed as indicated in FIG. 7A. The correlation coefficient (r) between the stored recombinant yeast GAD and porcine brain GAD immunoprecipitation results is high, 0.93. Comparability of results is optimal in the range of reliability of the RIP assay which is up to 100 units, beyond which titration of serum is required for precise quantification (Chen et al. 1993).

EXAMPLE 1

Figure 1:
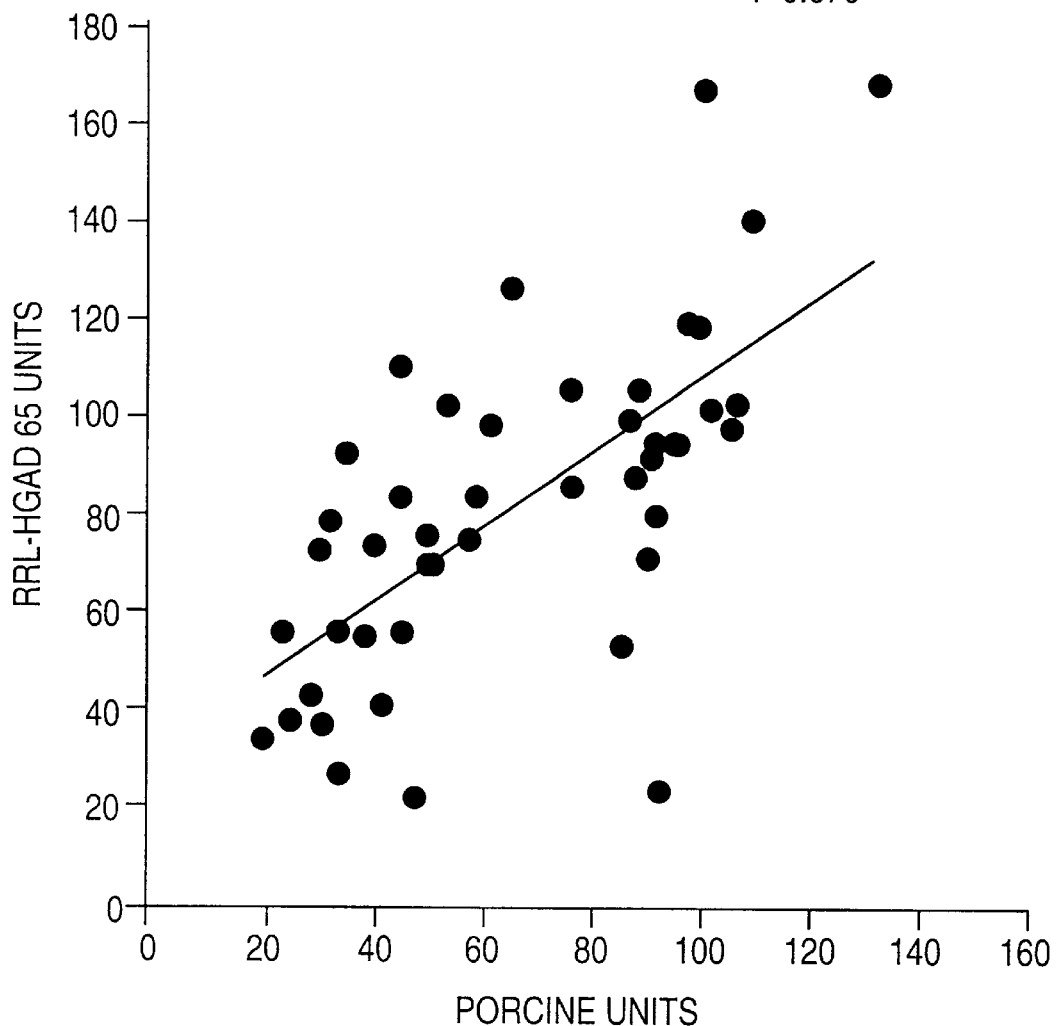
FIG. 1. Correlation of the reactivity of IDDM sera, as detected by immunoprecipitation, between purified porcine brain GAD and RRL expressed human brain GAD65. The correlation was significant ($p<0.005$).

This Example illustrates that hybrid GAD67/65 expressed by in vitro transcription and translation using rabbit reticulocyte lysate is as fully effective as GAD65 in immunoassays to demonstrate anti-GAD reactivity of serum in IDDM.

Materials and Methods

GAD cDNA Clones

Brain-derived cDNAs encoding human brain GAD65 and brain GAD67, and feline (F) brain GAD67 were gifts from Dr. A. Tobin. H-GAD65 and H-GAD67 were both contained in the Bluescript-SK vector (Stratagene, USA), designated as pBSGAD65 and pBSGAD67 respectively, under the control of the T3 promoter. The 1755 bp coding region of GAD65 was contained in a 2010 bp insert between the SacI and EcoRl cloning sites and the 1785 bp coding region of GAD67 was contained in a 2700 bp insert in the EcoRI cloning site. The 1878 bp F-GAD67 was encoded between the EcoRl and XbaI cloning sites of the pGEM4 vector (Promega, USA), designated as pGEM-F GAD67, under the control of the SP6 promoter.

A hybrid molecule was constructed consisting of combined regions of human brain GAD65 and GAD67, designated as GAD67(1–101)/GAD65(96–585) (hybrid GAD67/65), by replacing the region of cDNA encoding amino acids 1–95 of GAD65 with the region of cDNA encoding amino acids 1–101 from GAD67. The polymerase chain reaction (PCR) was used to amplify selectively the DNA sequence encoding amino acids 1–101 of GAD67. The sequence of the 5' oligonucleotide primer was (SEQ ID NO: 1) 5' TGGAGCTCATGGCGTCTTCGACCCCATCT 3' which incorporated a SacI restriction site at the 5' end. The sequence of the 3' oligonucleotide primer was (SEQ ID NO: 2) 5' TTCGCCGGCAGATCTCTAGCAAA 3' which incorporated a Bsr FI site at the 3' end without altering any amino acid sequence encoded by the H-GAD65 gene at the point of ligation. PCR using these 2 primers with pBSGAD 67 resulted in a product of 303 bp. The GAD65 in the Bluescript SK vector, pBSGAD 65, was prepared for the ligation of the GAD67 PCR fragment by first digesting with Sac I and then with Bsr FI. Due to the presence of multiple Bsr FI sites in the plasmid, ~5 µg of the SacI digested GAD65 plasmid was subjected to time course digest with 0.2 U of Bsr FI, aliquots were removed at 10, 20, 30, 40 and 60 minutes and examined by agarose gel electrophoresis. A 4.6 Kb DNA fragment of the digested product was recovered and ligated with the GAD67 PCR product. The resultant hybrid cDNA clone for GAD67/65$_1$ designated as pBSGAD67/65, was characterised by DNA sequence analysis. DNA sequencing of the fusion point between GAD65 and GAD67 in the resultant hybrid clone confirmed that the recombinant molecule had been formed correctly.

Production of GAD

GAD was expressed by in vitro transcription and translation using the rabbit reticulocyte lysate (RRL) system. Prior to transcription, plasmids pBSGAD65 and pBSGAD67/65 encoding human GAD65 and hybrid GAD67/65 respectively, were linearized at the 3' non-coding region using EcoR1 and plasmid pGEM-F-GAD67 was linearized with Xba I. Transcription of 1 µg plasmid DNA was in a 20 µl reaction mixture containing 40 mM Tris-HCl, pH 7.9, 6 mM MgCl$_2$, 2 mM spermidine, 10 mM dithiothreitol, 500 µM of each of ATP, GTP, CTP and UTP, 100 µg/ml BSA, 1000 U/ml RNAsin (Promega) and 600 U/ml of either T3 or SP6 RNA polymerase. This mixture was incubated for 60 minutes at 38° C. Transcription was stopped by the addition of 5 µl of 5 mM EDTA to the transcription mixture. A translation cocktail consisting of 200 µl nuclease treated RRL supplemented with 10 µl 1 mM amino acid mixture depleted of methionine, 40 µl [$^{35}$S-methionine (>1200 Ci/mmol) and 5 µl RNAsin (40,000 U/ml) was combined before addition to the transcription mixture. The translation reaction was incubated for 30 minutes at 30° C. After incubation, the mixture was centrifuged and the supernatant stored at −80° C. as 50 µl aliquots. Prior to use in the radioimmunoprecipitation assay, RRL translated GAD was passed through a NAP5 column (a Seogadex G-25 column made by Pharmacia Biotech) to separate the translation products from free [$^{35}$S]-methionine.

Sera

The sera studied were from 50 patients with IDDM diagnosed according to the criteria of the National Diabetes Data Group (1979). These sera were pre-selected according to positivity for autoantibodies to porcine brain GAD according to a radioimmunoprecipitation assay (see below). Controls were derived from a pool of sera from 50 healthy subjects.

Radioimmunoprecipitation Assay for anti-GAD Using Porcine Brain GAD

GAD was prepared from porcine brain by differential centrifugation and passage of the supernatant through an affinity column conjugated with the monoclonal antibody, GAD1. The ensuing preparation containing a mixture of GAD65 and GAD67 was labelled with $^{125}$I using the chloramine T procedure. These methods are described by Rowley et al, 1992.

Radioimmunoprecipitation Assay Using GAD Produced in RRL

Gel-purified GAD preparations obtained using RRL were "pre-cleared" with normal human sera (NHS) prior to assay. Two hundred µl of NHS was added to 200 µl of purified GAD and held for 60 minutes at 4° C. Two hundred µL of 50% Protein A Sepharose (Pharmacia, Sweden) suspended in wash buffer 120 mM Tris, 150 mM NaCl, 0.5% (w/v) Triton X-100, pH 7.4] was then added and held with the NHS and rabbit reticulocyte lysate-expressed GAD for 60 minutes at 4° C. The mixture was centrifuged for 2 minutes at 690×g and the supernatant was used as the source of antigen. Immunoprecipitation was performed by adding 40,000 DPM of "pre-cleared" GAD, 25 µl test sera and wash buffer in a total volume of 50 µl . After a 16 hr incubation at 4° C., 50 µl of 50% Protein A Sepharose was added and incubated for 60 minutes at 4° C. 1 ml of wash buffer was added to each of the samples, the samples were centrifuged for 2 minutes at 690×g, to pellet the Protein A Sepharose beads, and the supernatant was discarded. The pellets were washed an additional 3 times, then vortexed vigorously with 1 ml of scintillant and counted in a gamma counter.

Immunoprecipitated Form of Hybrid GAD67/65

The molecular weight of the hybrid GAD67/65 that was precipitated by IDDM sera was examined. After immunoprecipitation, the protein A Sepharose pellets were separated by SDS-PAGE on 10% gels under reducing and non-reducing conditions. The gels were fixed for 60 minutes in 50% (v/v) methanol, 10% (v/v) acetic acid, and then for 30 minutes in 5% (v/v) methanol, 10% (v/v) acetic acid, and immersed in Amplify solution (Amersham, UK) for 60 minutes before being dried onto filter paper under vacuum. The gels were overlayed with Fuji Medical X-Ray film (Fuji, Australia) in a cassette for 2 weeks at −80° C. before being developed.

Statistical Analysis

Data were analysed using the Complete Statistical System (StatSoft Inc, USA) computer program. Data were calculated as arithmetic means and standard deviations. The significance of differences was tested by Student's t-test for independent samples. Correlations were sought using the Pearson product moment correlation coefficient test.

Results

Reactivity of IDDM Sera with GAD of Differing Provenance

The frequency of reactivity by RIA of NHS and IDDM sera with recombinant GAD65 recombinant F-GAD67 and hybrid GAD67/65, all expressed in the rabbit reticulocyte lysate system, was determined and is shown in Table 1. The cut-off for a positive reaction for each antigen was defined as 3 standard deviations (SD) above the mean DPM precipitated by the NHS (Table 1). It is to be noted that these sera were pre-selected for reactivity by RIA with GAD purified from porcine brain. The frequency of positive reactions was 90%, 40% and 92% for GAD65, F-GAD67 and hybrid GAD67/65 respectively. Of the 40% of IDDM sera that reacted with F-GAD67, all reacted also with GAD65 and hybrid GAD67/65. Of 4 IDDM sera that did not react with hybrid GAD67/65, 2 did react with GAD65 but not F-GAD67, and 2 were entirely non-reactive.

TABLE 1

Results[1] of immunoprecipitation assays with normal human sera (NHS) and insulin-dependent diabetes mellitus sera (IDDM) using various sources of recombinant GAD expressed in the rabbit reticulocyte lysate system.

| GAD | n[3] | NHS mean (SD) | Cut-off x + 3SD | n[3] | IDDM mean (SD) | Positive[2] IDDM: NHS |
|---|---|---|---|---|---|---|
| GAD65 | 48 | 156 (55) | 321 | 50 | 1077 (444) | 90:0 |
| F-GAD67 | 45 | 182 (152) | 638 | 50 | 871 (794) | 40:2 |
| Hybrid GAD67/65[4] | 50 | 572 (107) | 893 | 50 | 4295 (1812) | 92:0 |

[1]Expressed as DPM in precipitate.
[2]Positive = % of cases > mean + 3SD for NHS.
[3]Number of cases tested.
[4]GAD67(1–101)/GAD65(96–585).

Figure 2:
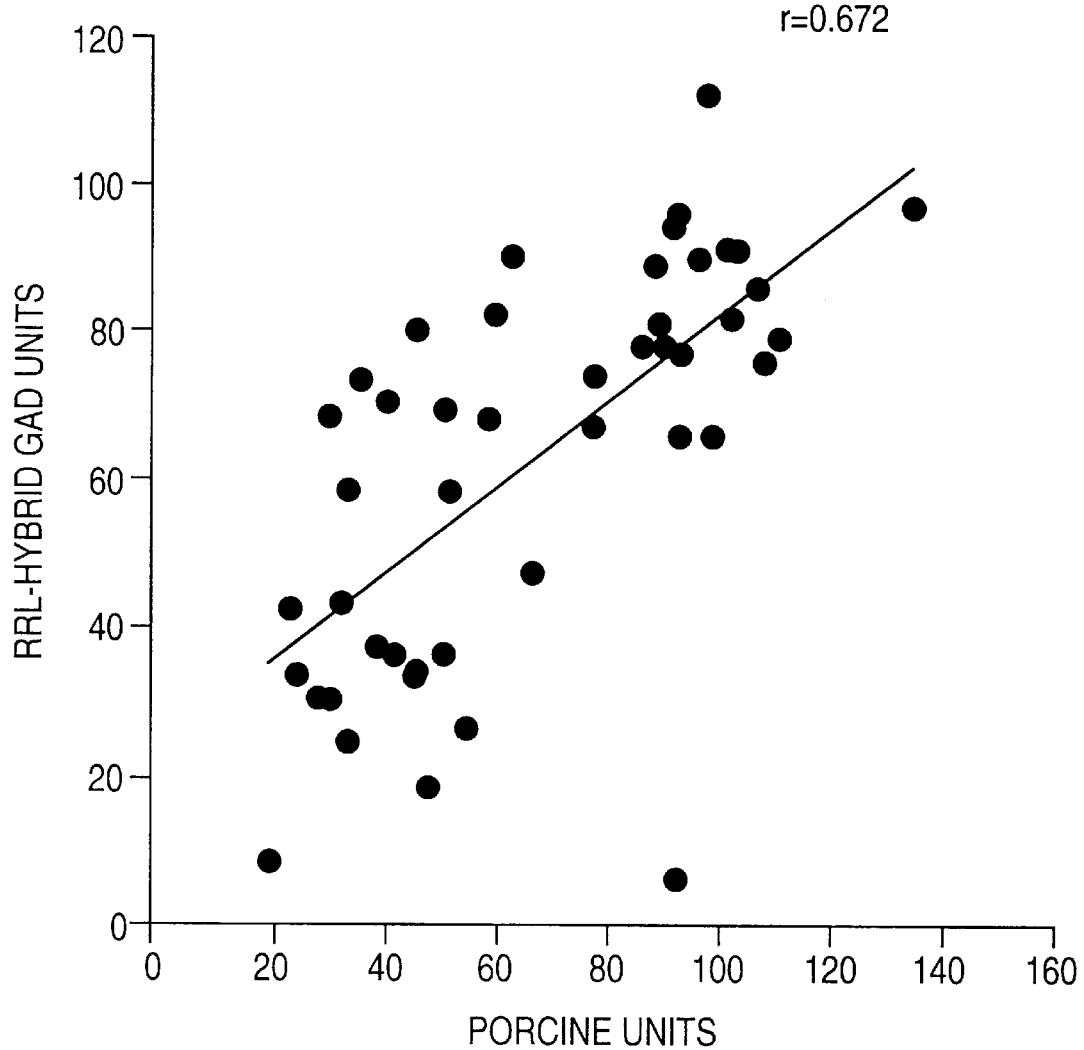
FIG. 2. Correlation of the reactivity of IDDM sera, as detected by immunoprecipitation, between purified porcine brain GAD and RRL expressed hybrid GAD67/65. The correlation was highly significant ($p<0.001$).

Correlations were sought for between reactivities of IDDM sera with preparations of GAD of differing provenance. Significant correlations were found for the reactivity of IDDM sera with purified porcine brain GAD and recombinant H-GAD65 (p<0.001, R=0.670)—see FIG. 1, between purified porcine brain GAD and hybrid GAD67/65 (p<0.001, R=0.6722)—see FIG. 2, and between recombinant H-GAD65 and hybrid GAD67/65 (p<0.002, R=0.675)—see FIG. 3. No correlations were found between reactivities of IDDM sera with porcine brain GAD and recombinant F-GAD67, recombinant GAD65 and recombinant F-GAD67, or hybrid GAD67/65 and recombinant F-GAD67.

Form of Hybrid GAD67/65 Precipitated by IDDM Sera

Figure 4A:
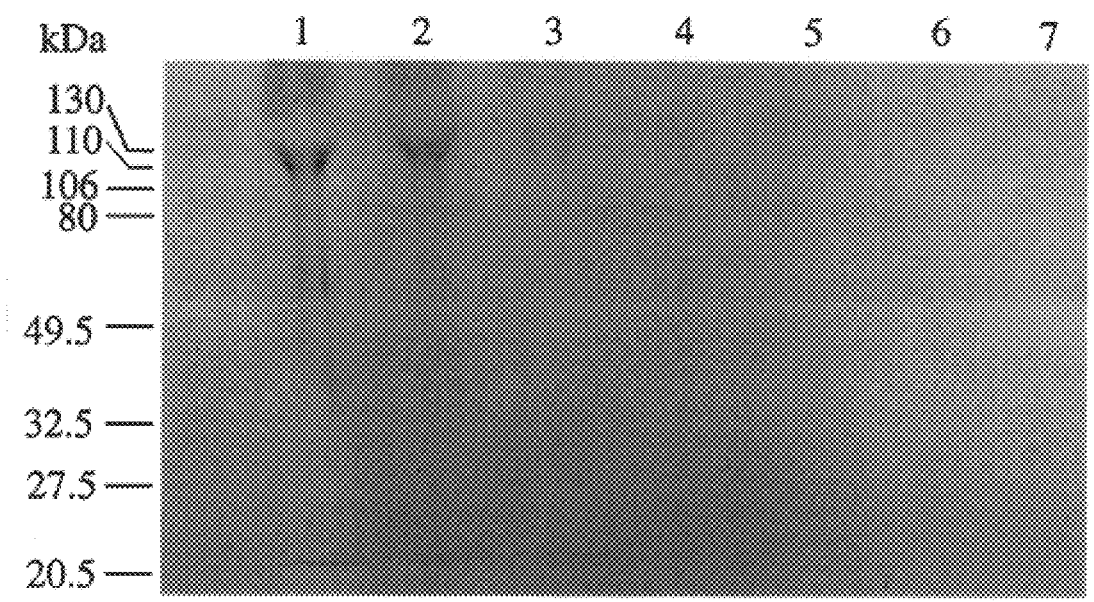
FIG. 4 Autoradiograph of a SDS-PAGE gel of protein A Sepharose pellets of IDDM and NHS after radioimmunoassay (RIA) with RRL expressed hybrid GAD67/65 separated under (a) non-reducing and (b) reducing conditions. Pellets of IDDM sera highly reactive by RIA with hybrid GAD67/65 are contained in lanes 1 and 2, weakly reactive with hybrid GAD67/65 in lane 3, and non-reactive NHS in lanes 4–7. Under non-reducing conditions, 2 bands of ~130 and 110 kDa are precipitated by IDDM sera which, under reducing conditions, reduced to ~65 and 45 kDa and smaller molecular weight bands. NHS did not precipitate either the 130 or 65 kDa band. The particular immunoreactivity of GAD with 130–110 kDa forms of the molecule under non-reducing conditions is described by Rowley et al. (1996).
Figure 4B:
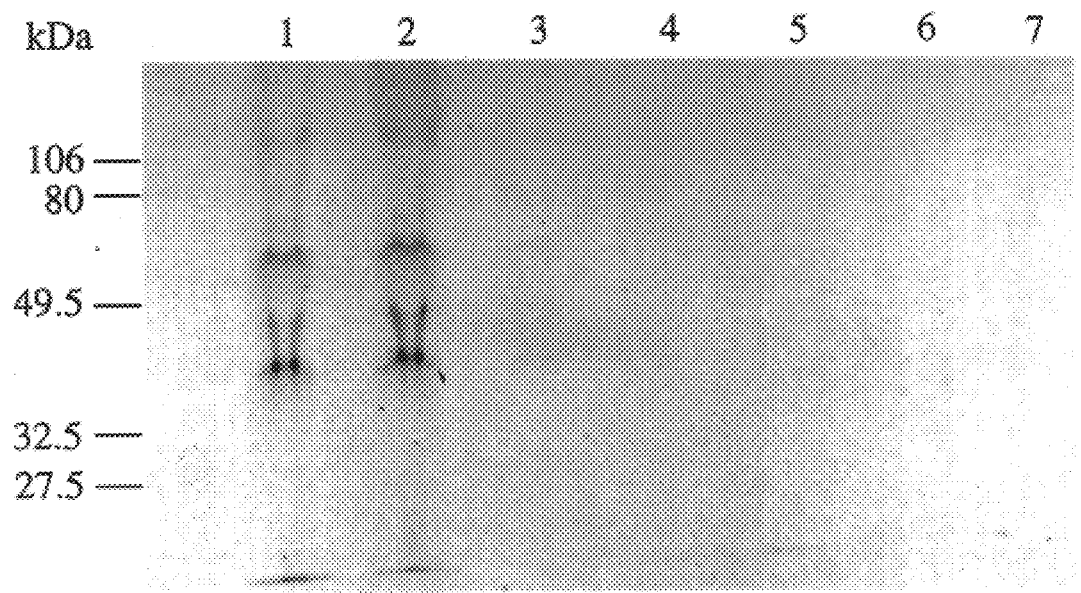

Hybrid GAD67/65 that was reactive with the sera of IDDM and normal subjects was examined by SDS-PAGE under reducing and non-reducing conditions and autoradiography. Protein-A Sepharose pellets obtained after immunoprecipitation with $^{35}$S-labelled hybrid GAD67/65 from 3 IDDM patients and 4 normal human subjects showed that under non-reducing conditions, IDDM sera precipitated 2 bands of ~130 and 110 kDa and under reducing conditions, in the presence of β-mercaptoethanol, these bands reduced to ~65 and 45 kDa (FIG. 4).

EXAMPLE 2

This Example shows the derivation of vectors for the expression of hybrid GAD67/65 in yeast, the purification of the expressed product by antibody affinity procedures, and the use of the radiolabelled product in radioimmunoprecipitation assays.

Materials and Methods

Microbial Strains and Vectors

*Escherichia coli* strain DH5α [recAI endA1 gyrA96 thi-1 relA1 SupE44 ΔlactU169 (φ80 lacZΔM15) hsdR17] was used for all sub-cloning purposes. *Saccharomyces cerevisiae* strain YRD15 (MATa ura3-2513-373, his3-11, leu2-3-11), a generous gift from Dr R. J. Devenish (Department of Biochemistry and Molecular Biology, Monash University, Clayton, Australia), was used for expression and purification of the human recombinant GAD. For most of the yeast expression experiments a construct based on plasmid pAS-1 was employed (see below for details), but in early studies a construct based on pYES2 (Invitrogen) was employed.

The yeast expression vector pAS-1, a derivative of pYEPLAC191 (Gietz and Sugino 1988), was obtained from Dr A. Stratton and Dr. R. J. Devenish (Department of Biochemistry and Molecular Biology, Monash University, Clayton, Australia). It contains the yeast phosphoglycerate kinase (PGK1) promoter and terminator elements to drive a high-level constitutive expression of heterologous genes, a 2 μm origin of replication to provide high copy number, and a LEU2 selectable marker to maintain the plasmid in the host strain (refer to FIG. 5).

A plasmid pMALGAL67/65 was derived from pBSGAD67/65 (see Example 1) by digestion of the plasmid pMALGAD67, containing the H-GAD67 cDNA in the EcoRl site of pMAL, with SalI and partially with NcoI. A 6243 bp fragment was purified and ligated to a 1876 bp fragment liberated by digestion of pBSGAD67/65 with SalI and NcoI. Thus, plasmid pMALGAD 67/65 was derived with a DNA sequence coding for maltose binding protein (MBP) fused to amino acids 1–101 of H-GAD67 which in turn are fused to amino acids 96–585 of H-GAD65 (hybrid GAD67/65).

Construction of pMONBC6, the Yeast Expression Vector pAS-1 Bearing the Hybrid GAD67/65.

Figure 5:
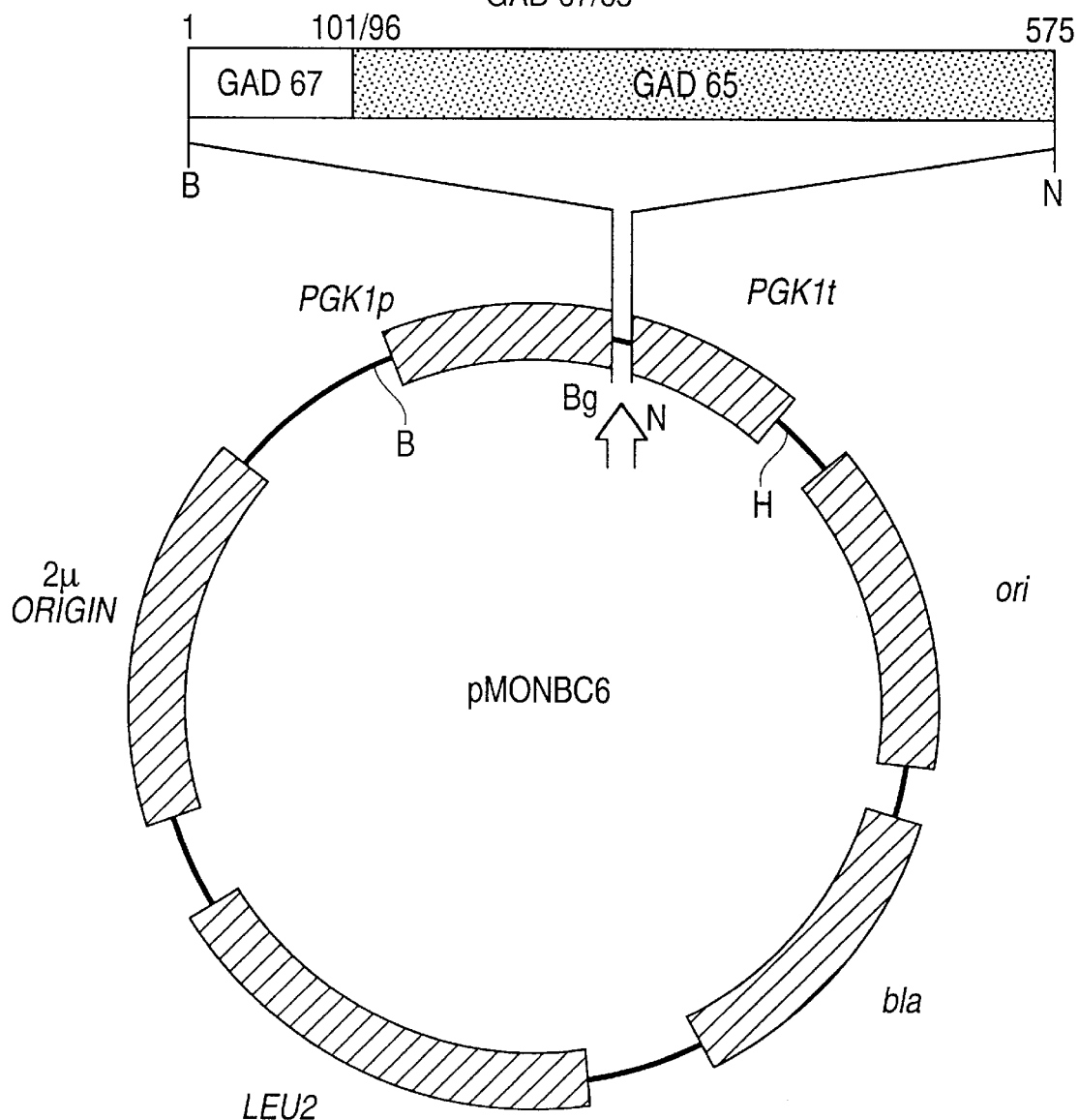
FIG. 5 Schematic illustration of pMONBC6. The black regions represent E. coli DNA sequences, including sequences specifying ampicillin resistance (bla) and the bacterial plasmid replication origin (ori). The grey regions represent yeast DNA sequences, including the yeast plasmid replication origin (2 µ), selectable marker LEU2 and transcriptional control sequences from the PGK1 gene, including the PGK1 promoter (PGK1p) and PGK1 terminator (PGK1t). The DNA sequence coding for hybrid GAD67/65, in which amino acid residues 1–101 of GAD67 is fused to amino acid residues 96–585 of GAD65 as illustrated, was cloned into the BamHI/NotI cloning site (shown as A) of the parent vector pAS-1 to generate pMONBC6. Abbreviations: B, BamHI; H, HindIII; Bg, BglII; N, NotI.

The construction of vectors for expression of hybrid GAD in yeast was accomplished in two stages. In the first stage, the hybrid GAD molecule was sub-cloned from pMALGAD67/65 into the EcoRI site of the inducible promoter system pYES2 to make pMONBC3. This plasmid, which carries the GAL1 promoter, was transformed into yeast YRD15, but the yield of recombinant hybrid GAD was low (data not shown). Hence, the plasmid pAS-1 containing the PGK1 promoter which provides a constitutive expression was tested. The BamHI-NotI fragment bearing the hybrid GAD67/65 gene was re-isolated from pMONBC3, and subcloned into the BglII-Notl site of pAS-1, to generate the plasmid pMONBC6 (FIG. 5).

Expression of Recombinant Hybrid GAD67/65 in *S. cerevisiae*.

The YRD15 strain was transformed with the plasmid pMONBC6 using a lithium acetate method (Elble, 1992). Transformants (YGAD-2) were selected on synthetic minimal glucose medium, SD+ura+his comprising 0.67% yeast nitrogen base without amino acid, 2% glucose, 20 mg/L uracil and 20 mg/L histidine. For expression, overnight cultures were grown up at 28° C. in liquid SD+ura+his medium with shaking, then diluted 1:50 into a selective medium (sacc) comprising 1 % yeast extract, 10% glucose, 20 mg/L uracil, 20 mg/L histidine, 0.12% $(NH_4)_2SO_4$, 0.1% $KH_2PO_4$, 0.07% $MgCl_2$, 0.05% NaCl, 0.01% $CaCl_2$ and 0.005% $FeCi_3$ and grown for a further 18–20 hours at 28° C. with shaking. The high glucose concentration was chosen to favour maximal induction of the PGK1 promoter. After growth, the cultures were harvested by centrifugation at 4° C. and used for enzyme purification. As a control, YRD15 was also transformed with the parent plasmid pAS-1 as above, and the resulting transformants (YpAS-1) as well as the yeast host YRD15 were used as negative controls in the studies of hybrid GAD expression in YGAD-2.

Purification of Recombinant Hybrid GAD67/65 from *S. cerevisiae*

A crude lysate of the yeast cells was obtained by vortexing the cells with equal volumes of glass beads (425–600 μm diameter) and lysis buffer (50 mM $KH_2PO_4$, 1 mM EDTA, 1 mM aminoethylisothiouronium bromide (AET), 20 μM pyridoxal phosphate (PLP), 10 mM 2-mercaptoethanol, 0.5 mM phenylmethylsulfonyl fluoride (PMSF) and 10 mM glutamate, pH 7.2), in six 30 second pulses, with 30 seconds on ice between pulses. The lysate was separated from the beads and intact cells by centrifugation, 5000 g for 5 min. The beads and the cell pellet were resuspended in another volume of lysis buffer, vortexed and centrifuged as above, and the lysate collected was combined with the first supernatant. The pooled lysate (S1) was clarified by centrifugation at 18,500×g for 10 min to generate S2 which was further clarified by ultra centrifugation, 100,000×g for 60 min. The supernatant collected was filtered through a 0.2 μm filter to remove any floating materials, to generate S3. Purification of recombinant hybrid GAD in S3 was by affinity chromatography using the monoclonal antibody GAD-1 (Chang and Gottlieb, 1988) conjugated to cyanogen bromide activated-Sepharose, as for purification of porcine brain GAD (Rowley et al., 1992). Recombinant hybrid GAD bound to the column was eluted into 1 ml fractions (F) with a high pH buffer (pH 10.5), and these were immediately neutralized to pH 7. A portion of the S1-3 and the flow through (S4) as well as all the eluted fractions were stored at −20° C. in 30% glycerol prior to their use in protein estimations and enzyme assays, other analytical studies including SDS-PAGE, immunoblotting, and iodination for immunoprecipitation.

Characterisation of Fractions Collected Throughout GAD Purification Process

Lysates (S1–S4) and purified fractions (F1–11 ) were analysed for the presence of recombinant hybrid GAD by SDS-PAGE and immunoblotting using the monoclonal antibody GAD-6 (Chang and Gottlieb, 1988) which reacts with the GAD65 isoform. The epitope for GAD-6 has been mapped to the C-terminal region of GAD65 (Daw and Powers, 1995); thus it was expected that GAD-6 would react with hybrid GAD67/65. GAD enzymatic activity was determined by a spin column chromatography procedure that uses the anion exchange resin (Bio-Rad AG® 1 -X8) to separate $^3$H-GABA from the more highly acidic $^3$H-glutamate, as described previously (Rowley et al., 1992). Protein concentration was determined by the Bradford dye-binding procedure (Bio-Rad Protein Assay) in accordance with the manufacturer's instructions.

Immunoprecipitation of Iodinated Recombinant Hybrid GAD67/65 by IDDM Sera

Immunoprecipitation of iodinated recombinant hybrid GAD67/65 by IDDM and non-IDDM sera was performed as described previously (Rowley et al., 1992). The 100 sera analysed were those submitted to the Second International GAD Antibody Workshop (Paris, France, 1994). The results obtained using the radio-iodinated yeast hybrid GAD67/65 were compared with those obtained using the standard preparation of porcine brain GAD from the laboratory (Rowley et al., 1992; Chen et al., 1993).

Results

Expression of Recombinant Hybrid GAD67/65 in YGAD-2

The expression of hybrid GAD67/65 in recombinant yeast YGAD-2 was studied by enzyme assay and Western blot on the crude cell lysate S1. Appreciable amounts of GAD protein and degrees of GAD enzyme activity were detectable. The results of the GAD enzyme activity in S1 prepared from the recombinant yeast YGAD-2, as well as all the controls YRD15 and YpAS-1 are shown in Table 2 . A high level of GAD enzyme activity was observed from the recombinant yeast, 8.4 nmol/min/mg, significantly higher than that from the yeast host YRD15, 0.68 nmol/min/mg, and the control YpAS-1, 0.73 nmol/min/mg. This level of enzyme activity is well above the levels reported previously for GAD in brain homogenates that have been widely used for GAD preparations; for example, that for human and pig brain homogenates was reported to be 0.124 and 2.4 nmol/min/mg, respectively (Blindermann et al., 1978; Spink et al., 1985), although the GAD enzyme activity in these brain homogenates might well vary significantly according to the freshness of the materials. The high level of GAD enzyme activity in the yeast lysates, as well as the ability to control the quality of the yeast material, are clear advantages of the GAD purification process from yeast.

TABLE 2

Purification of recombinant hybrid GAD expressed in *Saccharomyces cerevisiae*\*.

| Sample | Protein concentration (μg/ml) | Total Protein (mg) | Specific GAD enzyme activity (mmol/min/mg) | Total GAD enzyme activity (nmol/min) | % Recovery | Purification (fold) |
| --- | --- | --- | --- | --- | --- | --- |
| YGAD-2 | | | | | | |
| S1 | 5155 | 232 | 8.4 | 1949 | 100 | 1 |
| S2 | 4688 | 210 | 7.5 | 1579 | 81 | — |
| S3 | 4007 | 180 | 4.8 | 864 | 44.4 | — |
| S4 | 4176 | 188 | 0.6 | 113 | 5.8 | — |
| F1 | 0 | 0 | — | — | — | — |
| F2 | 2.34 | $3.5 \times 10^{-3}$ | 0 | — | — | — |
| F3 | 3.83 | $5.7 \times 10^{-3}$ | 0 | — | — | — |
| F4 | 5.6 | $8.4 \times 10^{-3}$ | 0 | — | — | — |
| F5 | 33.83 | $51 \times 10^{-3}$ | 2660 | 135 | — | — |
| F6 | 63.58 | $95 \times 10^{-3}$ | 2916 | 277 | — | — |
| F7 | 42.47 | $63 \times 10^{-3}$ | 2041 | 129 | — | — |
| F8 | 22.85 | $34.3 \times 10^{-3}$ | 829 | 28.4 | — | — |
| F9 | 7.1 | $10.7 \times 10^{-3}$ | 1021 | 10.9 | — | — |
| F10 | 9.18 | $13.8 \times 10^{-3}$ | 454 | 6.3 | — | — |
| F11 | 9.47 | $14.2 \times 10^{-3}$ | 212 | 3 | — | — |
| F (5–10)[1] | 29.84 | 0.27 | 1653 | 2.446 | 22.9 | 197 |
| YRD-15 | | | | | | |
| S1 | 4089 | 184 | 0.68 | — | — | — |
| S2 | 3760 | 169 | 0.6 | — | — | — |
| S3 | 3740 | 168 | 0.65 | — | — | — |
| YpAS-1 | | | | | | |
| S1 | 4076 | 212 | 0.73 | — | — | — |
| S2 | 4397 | 198 | 0.59 | — | — | — |
| S3 | 3823 | 172 | 0.85 | — | — | — |

\*10 ml harvested packed cells were lysed in the presence of glass beads. S1–S4 were generated as described in the methods, where S1 was collected after centrifugation at 5,000 g for 5 min to remove intact cells and glass beads; S2 was collected after the lysate was further clarified by centrifugation at 18,500 × g for 10 min, S3 was collected after ultracentrifugations at 100,000 × g for 2 × 60 min and filtration through a 0.2 μm membrane to remove floating material; S4 was assigned to the flow-through from the column chromatography using GAD-1. Recombinant hybrid GAD bound to the affinity column containing GAD-1 was eluted in 1 ml fractions (F1–11) of which the analysis of these 11 fractions (F1–11) is shown.
[1]F5–10 is a pool of F5 to F10.

Figure 6A:
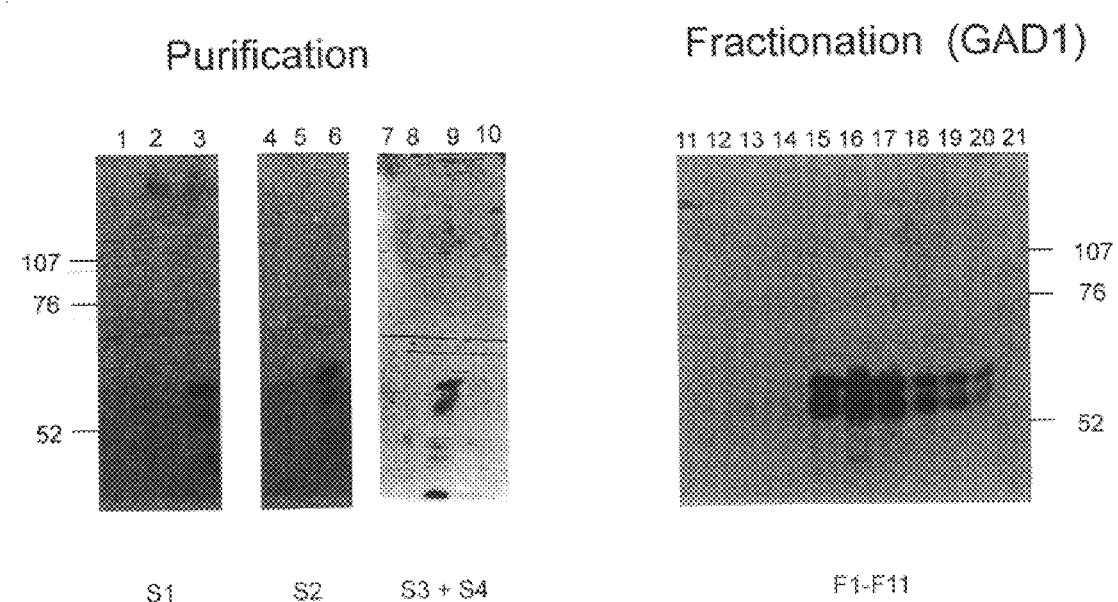

Using monoclonal antibody GAD-6 directed to GAD65 on Western blots has revealed at least two major GAD products in the yeast lysate from YGAD-2. One of those corresponded to 64 kDa, and the other to 60 kDa (FIG. 6A, lane 3). The 64 kDa product corresponded well to the full length of the hybrid GAD67/65 construct, whilst the 60 kDa product would represent an N-terminally truncated hybrid GAD product (see below). Based on the relative intensity of the two bands, the amount of the fall length product would be around 2–3 fold greater than that of the truncated product. A minor product corresponding to 45 kDa was also observed but its identity was not further investigated. Western blot analysis on cell lysates prepared from strains YRD15 and YpAS-1 showed no signal (FIG. 6A, lanes 1 and 2). Similarly, no signal was detectable on the culture medium in which YGAD-2 was propagated (data not shown).

These results of GAD enzyme activity and Western blot on S1 suggested that the recombinant hybrid GAD67/65 was expressed at a high level and with very high enzyme activity and, seemingly, was stable in the cytosol of the yeast host.

Purification of Recombinant Hybrid GAD67/65

Although there was an initial loss of GAD protein during its preparation from yeast lysate, a highly enzymatically reactive and pure preparation of GAD could be obtained by a single-step affinity chromatography, using the monoclonal antibody GAD-1. The procedure for purification of recombinant hybrid GAD from yeast was as described for porcine brain (Rowley et al., 1992). The amount of GAD recovered from various stages, S1–S4 and F1–F11, of the preparation of hybrid GAD was monitored by GAD enzyme assays, SDS-PAGE and Western blots. The results from a typical preparation are shown in Table 2 and FIG. 6A. Considering the enzyme activities (Table 2), there was a slight decrease of enzyme activity from 8.4 to 7.5 nmol/min/mg for S1 and S2, respectively. However for S3, there was a substantial decrease of the enzyme activity to 4.8 nmol/min/mg after the ultracentrifugation at 100,000 g. This loss of hybrid GAD during the ultra-centrifugation was regarded as a compromise for clarity of the lysate, which was essential for the column chromatography procedure. Nevertheless, this amount of GAD activity that remained in S3 is still twice as much as that reported for preparations from porcine brain, 2.4 nmol/min/mg (Spink et al., 1985)

As shown in Table 2, upon incubation with the GAD-1 antibody on the column, the enzyme activity became negligible in the flow through S4, 0.6 nmol/min/mg, showing that the recombinant yeast hybrid GAD bound efficiently to the GAD-1 antibody in the column. The immobilised recombinant hybrid GAD was eluted off the column with a pH 10.5 buffer, 1 ml fractions were collected and 0.5 g of glycerol was added to each fraction, as for S1–S4. The samples were kept at −20° C. before subsequent analyses were carried out. The results of analyses of the first 11 fractions (F1–11) collected were as follows. The purified yeast recombinant hybrid GAD was enzymatically highly reactive (Table 2), since the specific GAD enzyme activity was up to 2,916 nmol/min/mg in the peak fraction (F6). Pooling F5–10 gave a total yield of purified hybrid GAD of 270 $\mu$g with an average enzyme activity of 1,653 nmol/min/mg. The pooled F5–10 fractions, regarded as the net yield, represented a purification of 197 fold with a recovery of 22.9% of hybrid GAD in S1. Although the amount of hybrid GAD purified per run could be further improved, such as by increasing the capacity of the affinity column used, this enzyme activity, 1,653 nmollmin/mg, is very high compared with that of GAD purified from human brain which is 1,000 nmol/min/mg (Blindermann et al., 1978).

Studies on the control samples (S1–3) prepared from the yeast host (YRD15) and the yeast host transformed with the plasmid without the insert (YpAS-1) revealed negligible amounts of GAD enzyme activity (Table 2).

On Western blot analysis using the monoclonal antibody GAD-6, the amount of detectable hybrid GAD67/65 in S3 had decreased significantly compared with that of S1 and S2 (FIG. 6A, lanes 9, 3 and 6, respectively). This agrees well with results of the GAD enzyme activity assays, and suggests that ultra-centrifugation led to a significant loss of hybrid GAD from the lysate. It should be noted that the ratio of the 64 kDa to the 60 kDa proteins remained unchanged in samples S1–3. FIG. 6A also shows the results of Western blot analysis of the purified hybrid GAD (F1–F11, lanes 11–21). Recombinant hybrid GAD is detectable in F5–F10 (lanes 16–20), with F6 containing the highest level of hybrid GAD detectable (lane 17). This is in agreement with results of the specific enzyme activity assays (Table 2 ). The hybrid GAD products detectable represent as least two sizes, 64 and 60 kDa, as mentioned above. Interestingly, compared with the yeast lysates, the 60 kDa products in the purified samples had increased 34 fold over the 64 kDa product (FIG. 6A). The 40 kDa product observed previously was barely detectable.

The results of silver staining of SDS-PAGE analyses are shown in FIG. 6B. The hybrid GAD preparation is very pure (lanes 16–20), and F6 has the highest content of protein products. However, there are at least 5 distinct bands detectable, corresponding to molecular sizes, 64, 60, 59.5, 59 and 58.5 kDa. Previous studies in this laboratory have demonstrated that porcine GAD preparations are prone to N-terminal truncations, generating products from 65 to 55 kDa (Tuomi et al., 1994). Therefore it was expected that the yeast recombinant hybrid GAD was also truncated to yield a range of products of slightly lower molecular weight but with retained immunoreactivity. The Western blot analysis (FIG. 6A lanes 15–20) further suggests that truncation of the full length hybrid GAD occurs at the N terminal region of the protein, in that the GAD-6 monoclonal antibody used recognizes the C-terminal region of the GAD molecule, amino acids 529–586 (see above). It would be expected that all of the four truncated products, ranging in size from 60–58.5 kDa, would retain the GAD6 recognition domain, but this has yet to be ascertained since Western blot analysis using enhanced chemiluminescence (ECL) does not allow resolution of these four components into distinct bands. Importantly, either part or all of these purified hybrid GAD components are enzymatically highly reactive, and immunoprecipitable by IDDM sera (see below).

It would be desirable to prevent or limit the proteolysis that occurs during purification, by including protease inhibitors in the process. Two experiments thus far have been carried out to investigate whether the above mentioned lower molecular weight N-terminal truncation products of hybrid GAD67/65 can be limited by protease inhibitors. In the first experiment, a protease inhibitor cocktail (1 mg/ml Pefabloc SC, 3 $\mu$g/ml Leupeptin and 15 $\mu$g/ml Pepstatin) was included in the lysis buffer above; in the second, the composition of the cocktail was slightly different (25 $\mu$g/ml Aprotinin, 1 $\mu$/ml Leupeptin and 2.5 $\mu$g/ml Pepstatin A). These were ineffective in that the resulting GAD was found not to differ from untreated GAD with regard to enzyme activity, immunoreactivity on Western blot, or protein content as judged by SDS-PAGE. The next step would be determination of the specific type of proteases involved, for example by N-terminal sequencing of these truncated products.

Characterisation of Purified Recombinant Hybrid GAD67/65 by Reactivity to IDDM Sera The reactivity of the yeast hybrid GAD67/65 with IDDM sera was assayed by radioimmunoprecipitation assay using $^{125}$-labelled protein with a panel of 100 sera derived from the Second International GAD workshop (Paris, France, 1994). These sera had previously been tested in this laboratory using a preparation of GAD derived from porcine brain. As shown in FIG. 7A, there was very good agreement between the results obtained using yeast hybrid GAD67/65 and porcine brain GAD. All 55 sera identified as positive for anti-GAD using porcine brain GAD were also reactive to yeast hybrid GAD67/65, and all 45 sera identified negative for anti-GAD using porcine brain GAD were non-reactive using the yeast hybrid GAD. Thus, the yeast hybrid GAD67/65 and the porcine GAD when used in the standard radio-immunoprecipitation assay in this laboratory exhibited identical sensitivity and specificity for the diagnosis of IDDM.

Field Testing of Recombinant Hybrid Yeast GAD67/65

A preparation of recombinant yeast hybrid GAD67/65 has been "field-tested" as the standard reactant in radioimmunoassays for detection of anti-GAD in sera from control subjects, and in individuals with various types of diabetes mellitus and other diseases. In total, 5,068 individual serum assays have been performed in batches. These represent assays for purposes of research publications and medical diagnosis and have not been "controlled" by a comparison with an assay using an alternative form of GAD. Included in each assay batch were control sera that are known to react as low positive units for anti-GAD, and (c) high positive units for anti-GAD. Throughout the test period, the assay runs have given a true performance as judged by consistency of results with the control sera and by absence of anomalous results with the 5,068 test sera.

EXAMPLE 3

This Example illustrates that recombinant hybrid GAD67/65 produced in a yeast expression system retains stability when used as an immunoassay substrate (a) after labelling with radioactive iodine and (b) after retention in storage for periods up to two years at −20° C. Two of the purified samples with the highest content of GAD, from a yeast GAD preparation and fractionation as described in Example 2, were stored for two years at −20° C., radioiodine labelled and then compared for immunoreactivity by radioimmunoassay using a standard laboratory preparation of radiolabelled porcine brain GAD.

Materials and Methods

The sera used comprises 164 samples derived from normal subjects and patients with diabetes mellitus for which there was a known range of levels of anti-GAD, as judged by assays using radiolabelled purified porcine brain GAD.

The fractions used to assess effects of storage were those designated as F8 and F9 from a fractionation procedure performed as described in Example 2. These fractions were those most highly enriched for hybrid GAD67/65. The fractions were stored at −20° C. in 30% w/v glycerol for 2 years. Glycerol is added to prevent freezing and consequent degradation of GAD after thawing prior to use.

The fractions retrieved from storage were thawed and brought to room temperature and labelled with radioactive iodine. At the same time, a purified fraction from a freshly prepared hybrid GAD67/65 was also labelled with radioactive iodine.

Results

Two sets of comparisons are shown for three preparations of hybrid GAD67/65. The first comparison in Table 3 shows results using (1) the standard laboratory reference serum with a designated level of reactivity of 100 units, (2) a control "high positive" serum, (3) a control "low positive" serum, and (4) pooled normal human sera. This table shows counts of radioactivity precipitated, and the derived units of anti-GAD activity, for a preparation of freshly derived hybrid yeast GAD67/65, a preparation of hybrid yeast GAD67/65 stored at −20° C., and a fresh preparation of hybrid yeast GAD with a polyhistidine tag (see Example 4). The results are highly comparable for the three preparations, indicating that neither long storage at −20° C. nor the genetically engineered introduction of a polyhistidine tag (see below) has adverse effects on the immunoreactivity of yeast GAD.

TABLE 3

Comparison of antigenic reactivity of various preparations of recombinant hybrid yeast GAD67/65.

| | Preparation of Autoantigenic GAD[1] | | | | | |
|---|---|---|---|---|---|---|
| | "Fresh" Yeast GAD67/65[2] | | "Stored" Yeast GAD67/65[2] | | "Tagged" Yeast GAD67/65-H6[4] | |
| Serum Sample | cpm[5] | units | cpm | units | cpm | units |
| Anti-GAD reference serum designated as 100 units | 8824 | 100 | 8604 | 100 | 13934 | 100 |
| High positive anti-GAD serum | 8975 | 102 | 8654 | 100.5 | 14497 | 104 |
| Low positive anti-GAD serum | 2198 | 25 | 2878 | 33 | 4606 | 33 |
| Pooled normal human sera | 250 | 3.0 | 177 | 2.0 | 606 | 3.6 |

[1]Various preparations of radioiodine labelled yeast GAD were compared for reactivity with standard serum samples used for calibration of routine RIP assays for anti-GAD in this laboratory. These include the standard reference serum designated as containing 100 units of anti-GAD activity, a known high-positive serum, a known low-positive serum, and pooled normal human sera.
[2]"Fresh" yeast GAD67/65 was iodinated within 4 weeks of preparation; specific activity 25 µCi/µg.
[3]"Stored" yeast GAD67/65 was prepared and stored in 30% glycerol at −20° C. for 18 months prior to testing, specific activity on iodination was 22.6 µCi/µg.
[4]"Tagged" yeast GAD67/65 was a fresh preparation with a hexahistidine tag (see FIG. 8).
[5]cpm = counts of radioactivity precipitated in the radioimmunoassay.

Figure 7B:
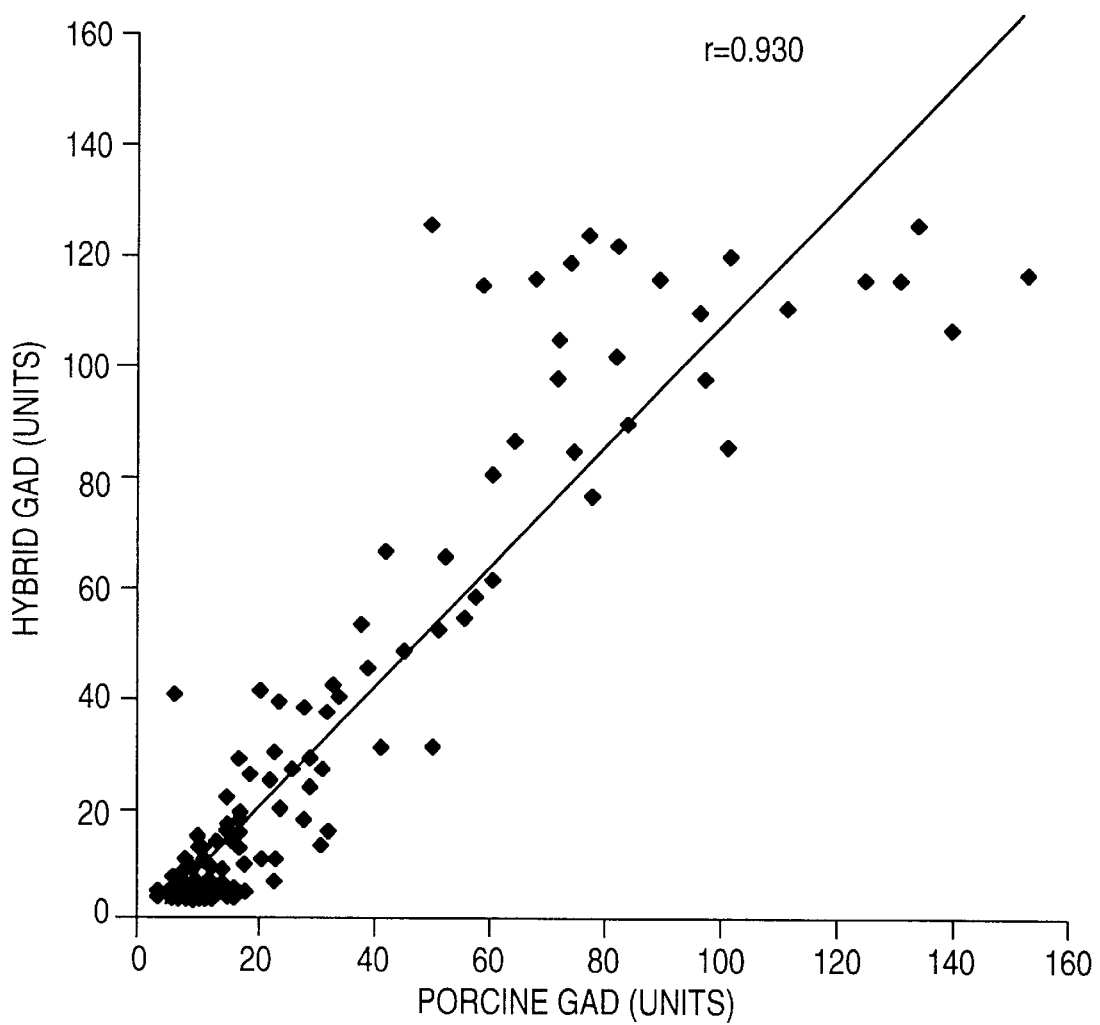
FIG. 7 A. Comparison of yeast hybrid GAD67/65 and purified porcine brain GAD by radio-immunoprecipitation. The sera tested were these submitted to the Second International GAD Workshop. Sera were analysed for the presence of antibodies to GAD by radioimmunoprecipitation. The results are expressed as reference units (Rowley et al., 1992) according to a standard reference serum, defined as containing 100 units. The correlation coefficient (r) between the recombinant yeast GAD and porcine brain GAD immunoprecipitation results is high, 0.94.

A comparison was made, using 164 sera from patients with diabetes mellitus with varying levels of anti-GAD, between radioimmunoassay results for purified porcine brain GAD and the yeast GAD preparation that had been retrieved from storage and labelled with radioactive iodine. These results are shown in FIG. 7B as a scatterplot. The close concordance of results is indicated by the correlation coefficient of 0.93. The correlation between immunoassay results for radioiodine labelled yeast GAD67/65 and porcine brain GAD is in fact higher than the correlation shown in FIG. 2 between biosynthetically labelled ($^{35}$S) yeast GAD and porcine brain GAD. It is evident from FIG. 7B that there is a divergence from a linear correlation plot for the highest levels of anti-GAD. This is in line with a known characteristic of the assay (Chen et al., 1993) for which, when there is antibody excess, titration of serum is required for a meaningful quantitative result.

EXAMPLE 4

This Example illustrates that hybrid GAD67/65 can be endowed with a C-terminal hexahistidine (H6) tag so that if desired the expressed gene product can be purified through metal matrix columns with affinity for the H6 tag, and that GAD67/65-H6 is enzymatically and antigenically equivalent to hybrid GAD67/65 purified by antibody-affinity columns.

Materials and Methods

Construction of GAD67/65-H6

A second hybrid molecule was constructed using the original hybrid GAD67/65 contained in the Bluescript-SK vector (Stratagene, USA), designated GAD67/65-H6. The polymerase chain reaction (PCR) was used to endow a C-terminal hexahistidine tag sequence on hybrid GAD67/65. The sequence of the 5' oligonucleotide primer was (SEQ ID NO: 3) 5' CCGGAATTCACCATGGCGTCTTCGACCCC3', which incorporated an EcoRI site at the 5' end but did not alter the amino acid sequence of GAD67/65. The sequence of the 3' primer was (SEQ ID NO: 4) 5 ' CCGGAATTCTTAGTG-GTGGTGGTGGTGGTGAGATAAATCTTGTTCAA GGCGTTCTATTTCTTC3', which also incorporated an EcoRI site at the 3' end after the sequence encoding the hexahistidine (H6) tag. A 1.8 kb DNA fragment encoding GAD67/65-H6 was recovered and digested with EcoRI, and sub-cloned into the Bluescript vector above. DNA sequencing of the resultant clone confirmed that the recombinant molecule had been formed correctly.

Construction of pMONTP1, the Yeast Expression Vector Bearing GAD67/65-H6

Figure 8:
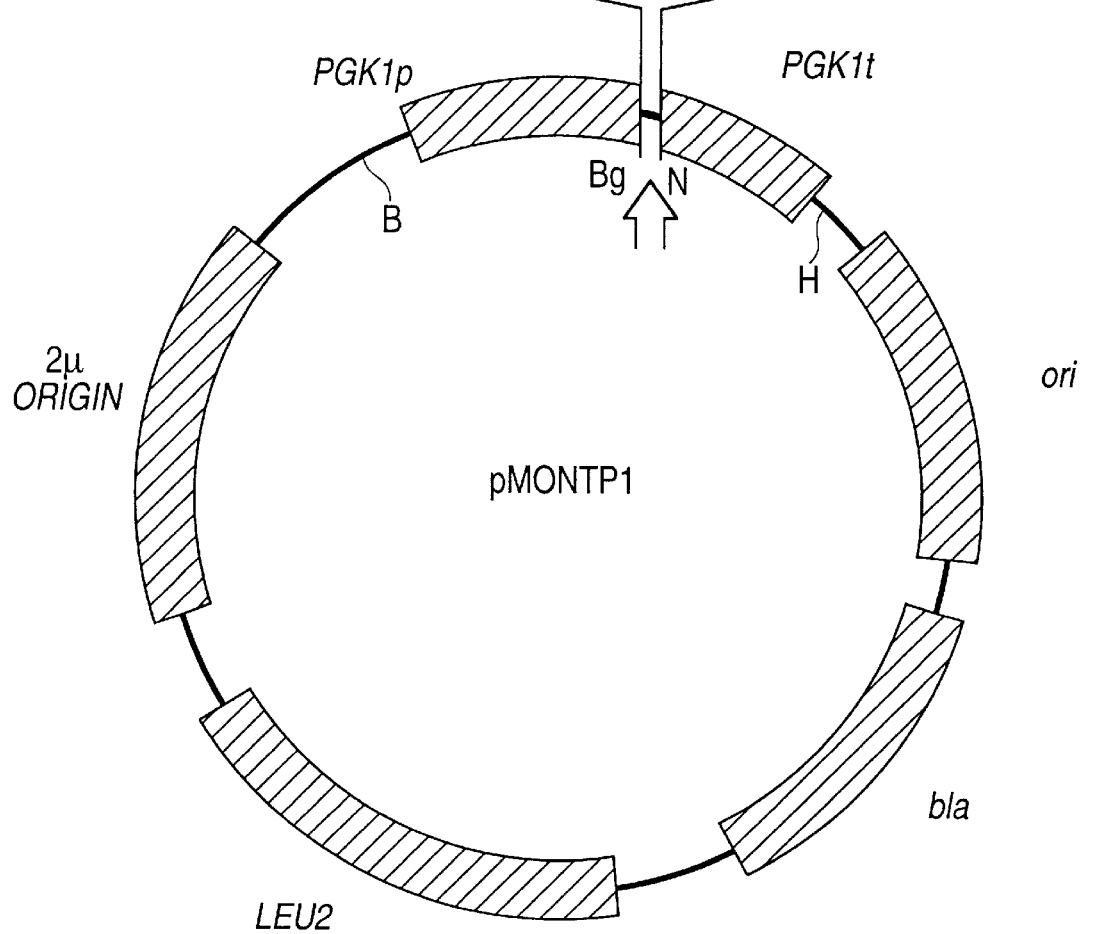
FIG. 8 Schematic illustration of pMONTP1. The coding for the construction of this vector, and abbreviations used, are as described for FIG. 5. Shown is the introduction at the 3' end of the cDNA for hybrid GAD67/65 of nucleotides encoding six histidine residues (hexahistidine tag)

The yeast expression vector pAS-1 was initially exposed to digestion with BglII, followed by generation of "blunt ends" by use of the Klenow fragment of DNA polymerase I and then digestion with the NotI restriction enzyme. The GAD67/65-H6 gene was isolated from the Bluescript vector as an EcoRV-NotI fragment, and subcloned into pAS-1, to generate the plasmid pMONTP1, as illustrated in FIG. 8.

Expression of GAD67/65-H6 in *S. cerevisiae*.

The YRD-15 strain was transformed with the plasmid pMONTP1 using the lithium acetate method (Elble, 1992). Transformants (YGAD-3) were selected and expressed for GAD production as for YGAD-2, which is the YRD-15 strain transformed with plasmid pMONBC6 and expressing the original recombinant hybrid GAD67/65.

Purification of GAD67/65-H6 from *S. cerevisiae*.

Purification of recombinant GAD from YGAD-3 was performed as for YGAD-2, except for a differing composition of the lysis buffer: this was 50 mM $KH_2PO_4$, 1 mM EDTA, 1 mM aminoethylisothiouronium bromide AET, 20 $\mu$M pyridoxal-L-phosphate PLP, 10 mM 2-mercaptoethanol, 10 mM glutamate, 0.12% (v/v) Triton X-100 and 0.5 mM phenylmethylsulfonyl fluoride (PMSF), pH 7.2.

Results

Expression of recombinant hybrid GAD67/65-H6 in YGAD-3.

The expression of GAD67/65-H6 in recombinant yeast YGAD-3 was performed in a manner very similar to that for GAD67/65 from YGAD-2. The results of the GAD enzyme assay for the crude yeast cell lysates did not reveal significant differences, these being 4.4 nmol/min/mg for GAD67/65 versus 3.6 nmol/min/mg for GAD67/65-H6. These were substantially higher than the enzyme assay results for a lysate of yeast host YRD-15, 0.68 nmol/min/mg, and the control yeast YpAS-1, 0.73 nmol/min/mg. Using the monoclonal antibody GAD-6 reactive with the C-terminal moiety on GAD65 by Western blot, two major GAD products in the yeast lysate from YGAD-3 are seen, with molecular weights of 64 and 60 kDa respectively, as for YGAD-2. After passage through the GAD-1 monoclonal antibody affinity column, the GAD67/65-H6 was purified as for GAD67/65. The yields were 0.18 mg of GAD67/65-H6 which compares well with 0.28 mg of GAD67/65, from equivalent 500 ml cultures of yeast. There was slightly higher enzyme activity in the pooled fractions for GAD67/65-H6 (4,654 nmol/min/mg). Purification levels were also very similar, 197-fold for GAD67/65 versus 239-fold for GAD67/65-H6.

Reactivity by Radioimmunoprecipitation After Labelling with Radioactive Iodine The introduction of a polyhistidine (H6) tag was shown not to influence the reactivity of recombinant hybrid yeast GAD67/65. Table 3 above shows results by radioimmunoprecipitation in counts of radioactivity precipitated, and conversion to assay units, for a fresh preparation of hybrid GAD67/65, a stored preparation of hybrid GAD67/65, and a preparation of hybrid GAD67/65-H6 after purification on an antibody affinity column. Data are presented for the standard reference serum designated as having 100 units of activity, a high positive anti-GAD serum, a low positive anti-GAD serum, and pooled normal human sera. It is seen that results are comparable for the three preparations.

EXAMPLE 5

This Example describes a preparation of recombinant hybrid yeast GAD67/65 that is purified and lyophilized in 1–2 mg quantities suitable for reconstitution in a vehicle in which GAD can be delivered to the upper intestinal tract of a strain of mice (non-obese diabetic, NOD, mice) prone to develop a disease that models human IDDM. This procedure, which is known as oral tolerogenesis, is a possible means of preventing or retarding the complete development of insulitis and diabetes in individuals in whom predictive immunoassay screening defines as being "at risk", i.e. in a presymptomatic incomplete stage of the disease.

Background

There is considerable interest among immunologists in the possibility that autoimmune disease in its earlier stages may be controlled by treatments that can "rewire" the immune system so that a state of damaging immune reactivity to autologous (self) components can be switched back to a normal state of tolerance to such components. This is demonstrably achievable by delivery of antigen to mucosal tissues, and more particularly the upper intestinal tract by the process of oral administration by feeding the antigen, hence called oral tolerance. Oral tolerance has been shown to be effective in various experimental animal models of autoimmune disease (Weiner, 1997). The principle has been applied to the prevention of diabetes in the NOD mouse using the autoantigens insulin and GAD. However these experiments do not provide any teaching on optimal preparations of GAD for use in human therapy for which GAD purified from mammalian brain would be clearly unsuitable, and recombinant GAD derived from currently used expression systems including rabbit reticulocyte lysate or mammalian cells would be too low in yield for long term treatment of humans at risk for IDDM.

Protocol

The protocol for the study requires that three groups (n=10) of female NOD mice are fed GAD in amounts of 20

μg, 10 μg and 5 μg twice weekly for 30 weeks. During this time, animals are assayed weekly for increased urinary glucose excretion and, when this is detected, blood glucose is measured. Appropriate control groups are included. The experiment ascertains whether feeding GAD using a particular formulation retards the natural development of diabetes in NOD mice whereby some 70–80% of untreated females develop the disease.

Results

This experiment is still in progress. It has been ascertained that hybrid yeast GAD67/65 can be lyophilized and reconstituted as a water-soluble preparation suitable for mucosal administration to mice. Preliminary observations are that the feeding of GAD has no adverse effects on mice. Moreover, there are no indications that oral administration of GAD accelerates the development of insulitis in NOD mice that are genetically predisposed to develop a disease that replicates many of the features of human IDDM.

Implications

The demonstration that orally administered hybrid yeast GAD67/65 can abrogate disease in the diabetes prone NOD mouse strain will have important implications for interventional therapy at the preclinical stage of human IDDM. In particular, the yeast system will provide for the relatively large amounts of GAD that will be needed for human use without recourse to GAD prepared from ammalian sources, and yeast as a common constituent of foods is a safe vehicle for preparation of recombinant GAD.

REFERENCES

1 Atkinson, M. A., N. K. Maclaren, D. W. Scharp, P. E. Lacy and W. J. Riley (1990). 64,000 Mr autoantibodies as predictors of insulin-dependent diabetes. *Lancet* 335:1357–1360.

2 Baekkeskov, S., H. J. Aanstoot, S. Christgau, A. Reetz, M. Solimena, M. Cascalho, F. Folli, H. Richter-Olesen, P. DeCamilli and P. D. Camilli, P. (1990). Identification of the 64K autoantigen in insulin-dependent diabetes as the GABA-synthesizing enzyme glutamic acid decarboxylase. *Nature* 347:151–156.

3 Baekkeskov, S., M. Landin, J. K. Kristensen, S. Srikanta, G. J. Bruining, T. Mandrup-Poulsen, C. deBeaufort, J. S. Soeldner, G. Eisenbarth, F. Lindgren et al. (1987). Antibodies to a 64,000 Mr human islet cell antigen precede the clinical onset of insulin-dependent diabetes. *J. Clin. Invest.* 79:926–934.

4 Blindermann, J. M., M. Maitre, L. Ossola and P. Mandel. (1978). Purification and some properties of L-glutamate decarboxylase from human brain. *Eur. J. Biochem.* 86:143–152.

5 Bu, D. F., M. G. Erlander, B. C. Hitz, N. J. Tillakaratne, D. L. Kaufman, C. B. Wagner-McPherson, G. A. Evans and A. J. Tobin. (1992). Two human glutamate decarboxylases, 65-kDa GAD and 67-kDa GAD, are each encoded by a single gene. *Proc. Natl. Acad. Sci. USA* 89:2115–2119.

6 Chang, Y. C. and D. I. Gottlieb, (1988). Characterization of the proteins purified with monoclonal antibodies to glutamic acid decarboxylase. J. Neurosci. 8:2123–2130.

7 Chen, Q. Y., M. J. Rowley, G. C. Byrne, T. W. Jones, T. Tuomi, W. J. Knowles, P. Z. Zimmett and I. R. Mackay. (1993). Antibodies to glutamic acid decarboxylase in Australian children with insulin-dependent diabetes mellitus and their first-degree relatives. *Pediatr. Res.* 34:785–790.

8 Daw, K. and A. C. Powers. (1995). Two distinct glutamic acid decarboxylase auto-antibody specificities in IDDM target different epitopes. Diabetes. 44:216–220.

9 Elble, R. (1992). A simple and efficient procedure for transformation of yeasts. *Biotechniques.* 13:18–20.

10 Erdo, S. L., Wolf, J. R. (1990). γ-aminobutyric acid outside the mammalian brain. *J. Neurochem.* 54:363–372.

11 Erlander, M. G. and Tobin A. J. (1991). The structural and functional heterogeneity of glutamic acid decarboxylase: a review. *Neurochem. Res.* 16:215–226.

12 Erlander, M. G., N. J. Tillakaratne, S. Feldblum, N. Patel and A. J. Tobin. (1991). Two genes encode distinct glutamate decarboxylases. Neuron. 7:91–100.

13 Faulkner-Jones, B. E., D. S. Cram, J. Kun et al. (1993). Localization and quantitation of expression of two glutamate decarboxylase genes in pancreatic β cells and other peripheral tissues of mouse and rat. Endocrinology 133:2962–2979.

14 Gietz, R. D. and A. Sugino. (1988). New yeast-*Escherichia coli* shuttle vectors constructed with in vitro mutagenized yeast genes lacking six-base pair restriction sites. *Gene* 74:527–534.

15 Grubin, C. E., T. Daniels, B. Toivola et al. (1994). A novel radioligand binding assay to determine diagnostic accuracy of isoform-specific glutamic acid decarboxylase antibodies in childhood. *Diabetologia* 37:344–350.

16 Guazzarotti, L., C. Thivolet, I. Tardivel, A. Chevalier, European Prediabetes Study Group and J. Carel. (1995). Reactivity of Islet Cell Antibodies (ICA) to Recombinant Glutamic Acid Decarboxylase (GAD). *J. Autoimmun.* 8:901–914.

17 Hagopian, W. A., B. Michelsen, A. E. Karlsen, F. Larsen, A. Moody, C. E. Grubin, R. Rowe, J. Petersen, R. McEvoy and A. Lernmark. (1993). Autoantibodies in IDDM primarily recognize the 65,000-M(r) rather than the 67,000-M(r) isoform of glutamic acid decarboxylase. *Diabetes* 42:631–636.

18 Karlsen, A. E., W. A. Hagopian, J. S. Petersen et al. (1992). Recombinant glutamic acid decarboxylase representing a single isoform expressed in human islets detects IDDM associated 64K autoantibodies. *Diabetes* 41:1355–01359.

19 Kaufman, D. L., M. G. Erlander, M. Clare-Salzler, M. A. Atkinson, N. K. Maclaren and A. J. Tobin. (1992). Autoimmunity in two forms of glutamate decarboxylase in insulin-dependent diabetes mellitus. *J. Clin. Invest.* 89:283–292.

20 Mauch, L., J. Seibler, H. Haubruck et al. (1993). Baculovirus-mediated expression of human 65 kDa and 67 kDa glutamic acid decarboxylases in Sf9 insect cells and their relevance in diagnosis of insulin dependent diabetes mellitus. *J. Biochem.* 113:699–704.

21 Michelsen, B. K., J. S.Pertersen, E. Boel et al. (1991). Cloning, characterization and autoimmune recognition of rat islet glutamic acid decarboxylase in insulin dependent diabetes mellitus. *Proc. Natl. Acad. Sci. USA* 88:8754–8758.

22 Myers, M. A., I. R. Mackay, P. Z. Zimmet and M. J. Rowley. (1996). Antibodies to Glutamate Decarboxylase in insulin Dependent Diabetes Mellitus. *Diabetes Annual* 10:15–36.

23 Petersen, J. S., K. R. Hejnaes, A. Moody et al. (1994). Detection of GAD65 antibodies in diabetes and other autoimmune diseases using a simple radioligand assay. *Diabetes* 43:459–467.

24 Powell, M. J., L. Prentice, T. Asawa, R. Kato, J. Sawicka, V. B. Petersen, A. Munkford, H. Tanaka, B. Rees Smith and J. Furmaniak (1995). High level expression of recombinant immunoreactive GAD65 in yeast. *Autoimmunity* 21:47.

25 Powell, M., L. Prentice, T. Asawa, R. Kato et al. (1996). Glutamic acid decarboxylase autoantibody assay using $^{125}$I-labelled recombinant $GAD_{65}$ produced in yeast. *Clinica Chimica Acta,* 256:175–188.

26 Richter, W., Y. Shiu and S. Baekkeskov. (1993). Autoreactive epitopes defied by diabetes-associated human monoclonal antibodies are localized in the middle and C-terminal domains of the smaller form of glutamate decarboxylase. *Proc. Natl. Acad. Sci. USA* 90:2832–2836.

27 Rowley, M. J., I. R. Mackay, Q. Y. Chen, W. J.Knowles and P. Z. Zimmet. (1992). Antibodies to glutamic acid decarboxylase discriminate major types of diabetes mellitus. *Diabetes* 41:548–551.

28 Rowley M. J., Q. Y. Chen, K. L. Teoh, P. Z. Zimmet, T. Tuomi, W. J. Knowles and I. R. Mackay (1996). Reactivity of glutamic acid decarboxylase with diabetes sera requires a dimeric-oligomeric form of the molecule. *Clin. Exp. Immunol.* 106:323–328.

29 Sambrook, J., E. F. Fritsch, and T. Maniatis, (1989). Molecular Cloning: A Laboratory Manual, 2nd Edn., Cold Spring Harbor, New York, Cold Spring Harbor Laboratory Press.

30 Seissler, J., J. Amann, H. Haubruck et at. (1993). Prevalence of autoantibodies to the 65 and the 67 kD isoforms of decarboxylase in insulin dependent diabetes mellitus. *J. Clin. Invest.* 92:1394–1399.

31 Solimena, M. F. Foli, R. Aparisi et al.. Autoantibodies to GABA-ergic neurons and pancreatic beta cells in Stiffman syndrome. *N. Engl. J. Med.* 322:1555–1560.

32 Spink, D. C. T. G. Porter, S. J. Wu and D. L. Martin. (1985). Characterization of three kinetically distinct forms of glutamate decarboxylase from pig brain. *Biochem. J.* 231:695–703.

33 Sudbery, P. E. (1996). The expression of recombinant proteins in yeasts. *Current Opinion Biotechnology* 7:517–524.

34 Tuomi, T., M. J. Rowley, W. J. Knowles, Q. Y. Chen, T. McAnally, P. Z. Zimmet and I. R. Mackay. (1994). Autoantigenic properties of native and denatured glutamic acid decarboxylase: evidence for a conformational epitope. *Clin. Immunol. Immunopathol.* 71:53–59.

35 Tuomilehto, J., P. Zimmet, I. R. Mackay, P. Koskela, G. Vidgren, L. Toivanen, E. Tuomilehto-Wolf, K. Kohtamaki, J. Stengard and M. J. Rowley. (1994). Antibodies to glutamic acid decarboxylase as predictors of insulin-dependent diabetes mellitus before clinical onset of disease (see comments). *Lancet* 343:1383–1385.

36 Ujihara, N. D. Daw, R. Gianani et al. (1994). Identification of glutamic acid decarboxylase autoantibody heterogeneity and epitope regions in type I diabetes. *Diabetes* 43:968–975.

37 Velloso, L. A., O. Kampe, A. Hallberg et al. (1993). Demonstration of GAD-65 as the main immunogenic isoform of glutamate decarboxylase in Type I diabetes and determination of autoantibodies using a radioligand produced by eukaryotic expression. *J. Clin. Invest.* 91:2084–2090.

38 Weiner, H. L. (1997). Oral tolerance: immune mechanisms and treatment of autoimmune diseases. *Immunology Today* 18:335–343.

---

We claim:

1. A hybrid glutamic acid decarboxylase (GAD) which comprises an amino-terminal moiety which comprises amino acid 1 to amino acid 90–105 derived from the human GAD67 isoform, said amino-terminal moiety being linked directly, or indirectly via an additional amino acid sequence, with a carboxy-terminal moiety which comprises amino acid 90–105 to amino acid 585 derived from the human GAD65 isoform.

2. A hybrid GAD according to claim 1, wherein said amino-terminal moiety comprises amino acid 1 to amino acid 95–101, of the human GAD67 isoform.

3. A hybrid GAD according to claim 1, wherein said carboxy-terminal moiety comprises amino acid 95–101 to amino acid 585, of the human GAD65 isoform.

4. A hybrid GAD according to claim 1, wherein the amino-terminal GAD67 moiety is linked directly to the carboxy-terminal GAD65 moiety.

5. A hybrid GAD according to claim 1, wherein the amino-terminal GAD-67 moiety is linked indirectly to the carboxy-terminal GAD65 moiety through a linker moiety of from 1 to about 50 amino acid residues.

6. A hybrid GAD according to claim 1, wherein the amino-terminal GAD67 moiety is linked indirectly to the carboxy-terminal GAD65 moiety through a linker of from 1 to about 20 amino acid residues.

7. A hybrid GAD according to claim 1, wherein the amino-terminal GAD67 moiety is linked indirectly to the carboxy-terminal GAD65 moiety through a linker moiety of from 1 to about 5 amino acid residues.

8. A hybrid GAD according to claim 1, which comprises amino acid residues 1 to 101 of the human GAD67 isoform linked directly to amino acid residues 96 to 585 of the human GAD65 isoform.

9. A hybrid GAD according to claim 1, further comprising an additional moiety coupled at one or both ends, said additional moiety being selected from a group consisting of a glutathione-S-transferase moiety, a β-galactosidase moiety and a hexa-His moiety.

10. An isolated nucleic acid molecule comprising a nucleic acid sequence encoding a hybrid GAD according to claim 1.

11. An isolated DNA molecule comprising a nucleic acid sequence encoding a hybrid GAD according to claim 1.

12. A recombinant DNA cloning vector comprising a nucleic acid sequence encoding a hybrid GAD according to claim 1.

13. A host cell comprising the vector of claim 11.

14. A host cell according to claim 11, which is a eukaryotic host cell.

15. A host cell according to claim 14 which is a yeast cell.

16. A host cell according to claim 15, which is a yeast cell selected from *Saccharomyces cerevisiae, Pichia pastoris, Kluyveromyces lactis, Hansenula polymorpha,* or *Schizosaccharomyces pombe.*

17. A method for the preparation of a hybrid GAD, which comprises expression of a nucleic acid sequence encoding a hybrid GAD according to claim 1, in a eukaryotic host cell, and recovery of the hybrid GAD.

18. A method according to claim 17, wherein the eukaryotic host cell is a yeast cell.

19. A method according to claim 18, wherein the yeast cell is selected from *Saccharomyces cerevisiae, Pichia pastoris, Kluyveromyces lactis, Hansenula polymorpha,* or Schizosaccharomyces pombe.

20. A method for the diagnosis and presymptomatic detection of IDDM in a human patient, characterised in that a hybrid GAD according to claim 1 is used to detect autoantibodies to GAD in serum taken from said patient.

21. A composition, comprising a hybrid GAD according to claim 1, together with one or more pharmaceutically acceptable carrier and/or diluents.

22. A composition according to claim 21 for mucosal administration.

23. A composition according to claim 22 for oral administration.

* * * * *

SEQUENCE LISTING

<160> NUMBER OF SEQ ID NOS: 4

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 1
tggagctcat ggcgtcttcg accccatct                                    29

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 2
ttcgccggca gatctctagc aaa                                          23

<210> SEQ ID NO 3
<211> LENGTH: 29
<212> TYPE: DNA
<213> ORGANISM: Artificial Sequence
<220> FEATURE:

```
<223> OTHER INFORMATION: Description of Artificial Sequence: Primer

<400> SEQUENCE: 3
ccggaattca ccatggcgtc ttcgacccc                                              29

<210> SEQ ID NO 4
<211> LENGTH: 63
<212> TYPE: DNA
<213> ORGANISM: Artificial Sequence
<220> FEATURE:
<223> OTHER INFORMATION: Description of Artificial Sequence: Primer

<400> SEQUENCE: 4
ccggaattct tagtggtggt ggtggtggtg agataaatct tgttcaaggc gttctatttc    60
ttc                                                                  63
```